United States Patent [19]

Bell et al.

[11] Patent Number: 5,606,085

[45] Date of Patent: Feb. 25, 1997

[54] THERMALLY ACTIVATED OLEFIN METATHESIS CATALYST PRECURSOR

[75] Inventors: Andrew Bell, West Grove, Pa.; Tim J. Coffy, Houston, Tex.

[73] Assignee: Metton America, Inc., Abingdon, Va.

[21] Appl. No.: 538,990

[22] Filed: Oct. 5, 1995

Related U.S. Application Data

[62] Division of Ser. No. 175,328, Dec. 29, 1993, Pat. No. 5,502,228.

[51] Int. Cl.$^6$ .............................. C07F 11/00; B01J 31/00
[52] U.S. Cl. .............................. 556/57; 502/152; 502/162
[58] Field of Search .............................. 556/57; 502/152, 502/162

[56] References Cited

U.S. PATENT DOCUMENTS

| | | | |
|---|---|---|---|
| 3,686,136 | 8/1972 | Doyle | 252/429 |
| 3,691,095 | 9/1972 | Kroll et al. | 252/428 |
| 3,849,513 | 11/1974 | Doyle | 260/683 |
| 4,400,340 | 8/1983 | Klosiewicz | 264/328.6 |
| 4,520,181 | 5/1985 | Klosiewicz | 525/247 |
| 4,681,956 | 7/1987 | Schrock | 556/12 |
| 4,727,215 | 2/1988 | Schrock | 585/645 |
| 5,142,073 | 8/1992 | Schrock et al. | 557/57 |

OTHER PUBLICATIONS

Schrock, R. R., "Metathesis Reactions Catalyzed by Well-Characterized Transition Metal Alkylidene Complexes", *The Strem Chemiker*, vol. XIV, No. 1, (Oct., 1992), pp. 1–6.

Schoettel, G. et al., "A Simple Route to Molybdenum–Carbene Catalysts for Alkene Metathesis", *J. Chem. Soc., Chem. Commun.*, (1989), pp. 1062–1063.

Oskam, J. H. et al., "Ligand Variation in Alkylidene Complexes of the Type Mo(CHR) (NR') (OR")$_2$", *J. Organometallic Chemistry*, 459 (1993), pp. 185–198.

Fox, H. H. et al., "Synthesis of Five–and Six–Coordinate Alkylidene Complexes of the Type Mo(CHR) (NAr) [OCMe (CF$_3$)$_2$]$_2$S$_x$, and Their Use as Living ROMP Initiators or Wittig Reagents", *Organometallics*, 12 (1993), pp. 759–768.

Nugent, W. A. et al., "Reaction of Group 6 Organoimido Complexes with Organozinc, Reductive Elimination Across a Metal–Nitrogen Multiple Bond", *J. Amer. Chem. Soc.*, 102 (1980), pp. 1759–1760.

Quignard, F. et al., "Synthesis and Catalytic Properties of W(OAr)$_2$Cl$_2$ (CHCMe$_3$) (OR$_2$) and W(OAr)$_2$Cl (CHCMe$_3$) (CH$_2$CMe$_3$) (OR$_2$) (Ar=2,6–disubstituted phenyl; R=Et or Pr$^i$), New Unicomponent Catalysts for Metathesis of Acyclic and Cyclic Olefins, with or without Functional Groups", *J. Chem. Soc., Chem. Commun.*, (1985), pp. 1816–1817.

Kress, J. et al., "Tungsten (IV) Carbenes for the Metathesis of Olefins. Direct Observation and Identification of the Chain Carrying Carbene Complexes in a Highly Active Catalyst System", *J. Chem. Soc. Chem. Commun.*, (1982), pp. 514–516.

Schrock, R. R. et al., "Synthesis of Molybdenum Imido Alkylidene Complexes and Some Reactions Involving Acyclic Olefins", *J. Am. Chem. Soc.*, 112 (1990), pp. 3875–3886.

Fu, G. C. and Grubbs, R. H., "The Application of Catalytic Ring–Closing Olefin Metathesis to the Synthesis of Unsaturated Oxygen Heterocycles", *J. Am. Chem. Soc.*, 114 (1992), pp. 5426–5427.

Kress, J. and Osborn, J. A., "Tungsten Carbene Complexes in Olefin Metathesis: A Cationic and Chiral Active Species", *J. Am. Chem. Soc.*, 105 (1983), pp. 6346–6347.

Schrock, R. R. et al., "Further Studies of Imido Alkylidene Complexes of Tungsten, Well–Characterized Olefin Metathesis Catalysts with Controllable Activity", *Organometallics*, 9 (1990), pp. 2262–2275.

Quignard, F. et al., "Aryloxide Ligands in Metathesis of Olefins and Olefinic Esters: Catalytic Behaviour of W(OAr)$_2$Cl$_4$ Complexes Associated with Alkyl–Tin, or Alkyl–Lead Co–catalysts; Alkylation of W(OAr)$_2$Cl$_4$ by SnMe$_4$, Sn(n–Bu)$_4$, Pb(n–Bu)$_4$, Mg Np$_2$: Synthesis of W(OAr)$_2$Cl$_2$ (CHCMe$_3$) (OR$_2$) and W(OAr)$_2$Cl (CHCMe$_3$) (CH$_2$CMe$_3$) (OR$_2$)", *J. Molecular Catalysis*, 36 (1986), pp. 13–29.

Muetterties et al., "Olefin Metathesis Reaction: Characterization of an Active Catalyst Precursor, CH$_3$WOCl$_3$·O(C$_2$H$_5$)$_2$, from the WOCl$_4$—(CH$_3$)$_2$Mg Reaction", *J. Am. Chem. Soc.*, vol. 102, No. 21 (1980) pp. 6572–6574.

Kress et al., "Tungsten (VI) and Molybdenum (VI) Oxo–alkyl Species. Their Role in the Metathesis of Olefins", *J.C.S. Chem. Comm.*, No. 10, (1980) pp. 431–432.

Kress et al., "Molecular Complexes for Efficient Metathesis of Olefins, The Oxo–ligand as a Catalyst–Cocatalyst Bridge and the Nature of the Active Species", J.C.S. Chem. Comm., No. 20, (1981) pp. 1039–1040.

*Primary Examiner*—Porfirio Nazario-Gonzalez
*Attorney, Agent, or Firm*—Fitzpatrick, Cella, Harper & Scinto

[57] ABSTRACT

Molybdenum and tungsten compounds that are useful as catalyst precursors in the metathesis of olefins have the general formula:

$$M(Y)(OR^2)_x(R^3)_y(X)_zL_s$$

wherein M is tungsten or molybdenum; Y is oxygen or NR$^1$; R$^1$, R$^2$, and R$^3$ are the same or different and are selected from alkyl, cycloalkyl, cycloalkenyl, polycycloalkyl, polycycloalkenyl, haloalkyl, haloaralkyl, substituted or unsubstituted aralkyl and aryl groups, and silicon-containing analogs thereof; L is a Lewis base; X is halogen; s is 0 or 1; x+y+z=4, and y≧1, provided that when x is 2 or more, two OR$^2$ groups can be replaced by a chelating ligand (OR$^2$)$_2$.

These compounds can be used for the metathesis of olefins in neat metathesizable olefin, as well as in solution, and require only the input of energy to be converted to active catalysts.

34 Claims, No Drawings

THERMALLY ACTIVATED OLEFIN METATHESIS CATALYST PRECURSOR

This application is a division of application Ser. No. 08/175,328 filed Dec. 29, 1993, now U.S. Pat. No. 5,502,228.

FIELD OF THE INVENTION

This invention relates to tungsten and molybdenum compounds that are useful as catalyst precursors for olefin metathesis reactions, and to novel methods for synthesizing these compounds. This invention also relates to new molding techniques using olefin metathesis catalyst precursors.

BACKGROUND OF THE INVENTION

The olefin metathesis process can be defined as the redistribution of alkylidene moieties to give a mixture of olefins, e.g., propylene is converted to ethylene and butylene. The simplest example is:

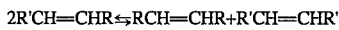

The reaction proceeds by addition of an olefin to a catalyst having a metal-carbon double bond ([M]=CHR; metal alkylidene complex) to give a metallacyclobutane ring, which then releases an olefin to reform a metal-alkylidene complex. A typical olefin of interest that will undergo metathesis in the presence of an appropriate catalyst is an ester of oleic acid, cis-$CH_3(CH_2)_7CH=CH(CH_2)_7CO_2H$.

Ring-opening metathesis polymerization (ROMP) of cycloolefins by olefin metathesis catalysts is an extremely important facet of the olefin metathesis reaction that results in the preparation of thermoset and thermoplastic polymers. Monocyclic olefins, substituted monocyclics, polycyclic and substituted polycyclic olefins have all been employed in the preparation of unsaturated polymers. In many cases, cycloolefins can be polymerized even when they contain polar or reactive functional groups. Norbornene is a typical olefin that will undergo ROMP in the presence of an olefin metathesis catalyst having a metal-carbon double bond.

A third type of olefin metathesis reaction is acyclic diene metathesis (ADMET). ADMET chemistry can be used to form dimers, oligomers, or polymers. ADMET polymerization is a viable synthetic route to high molecular weight polymers and copolymers, but it is an inherently more complicated process than ring-opening metathesis polymerization (ROMP). ROMP is a chain growth, addition-type polymerization driven by the alleviation of ring strain. The ADMET reaction is a step propagation condensation reaction. The ADMET reaction is an equilibrium process wherein the product is generated by the removal of an olefin, typically ethylene, from the reaction. Thus, in the ADMET (or simple olefin metathesis) reaction of styrene (a monoolefin), quantitative metathesis chemistry occurs yielding the expected dimer of trans-stilbene. At high conversion, ADMET polymerization of 1,9-decadiene (an α, ω-diolefin) yields poly(octylene). When ADMET polymerization reactions are terminated before reaching ≈99% conversion, the α, ω-diolefins employed generate oligomers, since step growth polymerization only produces high molecular weight polymer at very high conversions. An important aspect of ADMET polymerization is that ester and ether functionalities are often tolerated on the time scale of the polymerization reaction, and polymers can be prepared that are not directly available in a ROMP reaction.

Because the ADMET reaction is a step growth equilibrium condensation reaction, it provides the opportunity to shift the equilibrium between monomer and polymer. It has been found that unsaturated polymers, such as polynorbornene and polybutadiene, can be depolymerized in combination with ethylene to yield low molecular weight oligomers and α, ω-alkadienes.

The olefin metathesis reaction has also been employed in ring-closing metathesis of acyclic diene ethers to form cyclic and acyclic olefins (Fu and Grubbs, *J. Am. Chem. Soc.* 1992, Vol. 114, p. 5426–27). For example, various diallyl ethers when treated with a well-defined alkylidene complex, $Mo(CHCMe_2Ph)$ $(NC_6H_3-2,6-i-Pr_2)$ $(OCMe(CF_3)_2)_2$, lead to a number of ring-closed derivatives, i.e., cyclic ethers, amines and amides.

To reap the benefits of functionalized olefin metathesis, ring-opening metathesis, ring-closure chemistry, and the ADMET chemistry described above, the trend has been towards the formation of less Lewis acidic, well-characterized catalyst species based on a variety of transition metals including tungsten and molybdenum. These catalysts should be simple to prepare, of known structure, and with a reactivity that can be controlled. Several of these types of compounds have been shown to metathesize olefins with an activity that can be regulated through the choice of aryloxide or alkoxide ligands. For examples, see J. M. Basset et al., *Angew. Chem.*, 1992, Vol. 104, p. 622–664; J. A. Osborn et al., *J. Chem. Soc.*, Chem. Commun., 1989, p. 1062–1063; R. R. Schrock, U.S. Pat. Nos. 4,681,956 and 4,727,215, and R. R. Schrock et al., U. S. Pat. No. 5,142,073.

Tungsten and molybdenum catalysts, $M(=CHR^3)$ $(NR^t)$ $(OR^2)_2$, reported by R. R. Schrock have been employed in all of the areas of olefin metathesis described above. These well-defined transition metal alkylidene complexes have a high tolerance for functionalized groups as well as temperature. Molybdenum and tungsten alkylidene complexes of the following compositions are particularly useful: $Mo(CHCMe_2Ph)$ $(NC_6H_3-2,6-i-Pr_2)$ $(OCMe(CF_3)_2)_2$, $Mo(CHCMe_3)$ $(NC_6H_3 2,6-i-Pr_2)$ $(OCMe_3)_2$, $Mo(CHCMe_3)$ $(NC_6H_3-2,6-i-Pr_2)$ $(OCMe(CF_3)_2)_2$, $W(NC_6H_3-2,6-i-Pr_2)$ $(CHCMe_2Ph)$ $(OCMe_3)_2$, $W(NC_6H_3-2,6-i-Pr_2)$ $(CHCMe_3)$ $(OCMe_3)_2$, $W(NC_6H_3-2,6-i-Pr_2)$ $(CHCMe_2Ph)$ $(OCMe(CF_3)_2)_2$ $W(NC_6H_3-2,6-i-Pr_2)$ $(CHCMe_3)$ $(OCMe(CF_3)_2)_2$, $W(NC_6H_3-2,6-i-Pr_2)$ $(CHCMe_2Ph)_2(OCMe(CF_3)_2)_2$, and $W(NC_6H_3-2,6-i-Pr_2)$ $(CHCMe_3Ph)_2(OC(CF_3)$ $(CF_2CF_3)_2$. These catalysts, however, are typically prepared using multistep synthetic routes that are quite labor intensive and often use expensive reagents.

The simple olefin metathesis reaction and ring-opening metathesis polymerization synthesis of specialty polymers using these catalysts are performed in homogeneous phase by reacting the olefin with the alkylidene species in a solvent. The ADMET reaction employing these catalysts can be performed both in solution and in bulk monomer.

In the manufacture of thermoset polymers, it is desirable to have a solventless system so that solvent is not trapped within the polymer matrix. One disadvantage to the use of well-defined alkylidene catalysts is that they initiate polymerization (or olefin metathesis) immediately upon contact with a metathesizable monomer.

Reaction injection molding (RIM) of polyolefins by ring-opening of polyolefin metathesis polymerizable monomers in the presence of alkylidene complexes is a particularly important aspect of olefin metathesis. For example, Klosiewicz (U.S. Pat. Nos. 4,400,340 and 4,520,181) discusses a method whereby polydicyclopentadiene can be prepared by combining a plurality of reactant streams. One stream contains a metathesis catalyst and the second stream the activator for the metathesis system, and at least one contains dicyclopentadiene. After mixing the streams and generating a metathesis catalyst, the mixture is immediately injected into a mold where polymerization takes place. Although such catalysts are very effective species for polymerization, residual amounts of chlorine or solvent for the dissolution of the catalyst precursor or activator are retained in the thermoset product.

SUMMARY OF THE INVENTION

A family of olefin metathesis catalyst precursors has been discovered whose members are regarded as unicomponent catalyst precursors, since they require no chemical activator. The use of Lewis base rate moderators in this system is optional.

Specifically, this invention relates to the generation of olefin metathesis catalysts by thermal activation or activation by some other energy input of single compounds (olefin metathesis catalyst precursors) or mixtures of catalyst precursors. This activation can occur in a solvent or in an olefin metathesizable monomer. The catalyst precursors of this invention comprise transition metal-based compounds that provide facile conversion to the corresponding olefin metathesis catalysts.

Such catalyst precursors can be represented by the following structural formula:

$$M(Y)(OR^2)_x(R^3)_y(X)_zL_s \qquad (I)$$

wherein M is molybdenum or tungsten; Y is oxygen or $NR^1$; $R^1$, $R^2$, and $R^3$ are selected from alkyl, cycloalkyl, cycloalkenyl, polycycloalkyl, polycycloalkenyl, haloalkyl, haloaralkyl, substituted or unsubstituted aralkyl and aryl groups, and silicon-containing analogs thereof; X is halogen; L is a Lewis base; s=0 or 1; +y +z=4, and y≧1, provided that when x is 2 or more, two $OR^2$ groups can be replaced by a chelating phenolate, catecholate, binaphtholate or chelating alcoholate ligand $(OR^2)_2$, e.g., pinacolato, benzopinacolato, and glycolate ligands.

These olefin metathesis catalyst precursors have proven useful in homogeneous, solventless olefin metathesis polymerization reactions. They are especially useful in the bulk ring-opening metathesis polymerization of mono- and polycyclic olefins (ROMP), especially norbornene, substituted norbornenes, dicyclopentadiene and higher polycyclic olefins. Both thermoset and thermoplastic polymers can be prepared. The olefin metathesis catalyst precursors are also useful in the depolymerization of unsaturated polymers, especially thermoset resins. The catalyst precursors can also be used for simple metathesis of olefins, acyclic diene metathesis (ADMET), and ring closure reactions.

In addition, the present invention also encompasses within its scope novel methods for the preparation of one particular class of metathesis catalysts having the following formula (II): $M(=CHR^4)(NR^1)(OR^2)_2L_s$, wherein M is molybdenum or tungsten; $R^1$ and $R^2$ are the same or different and are selected from alkyl, cycloalkyl, cycloalkenyl, polycycloalkyl, polycycloalkenyl, haloalkyl, haloaralkyl, substituted or unsubstituted aryl and aralkyl groups, and silicon-containing analogs thereof; $R^4$ is an alkyl, aryl, or aralkyl group or any substituent that results from the initial reaction between the $M=CHR^4$ complex and the olefin that is to be metathesized. When $R^3$ is a cycloalkyl, polycycloalkyl, cycloalkenyl, or polycycloalkenyl group, then $(=CHR^4)$ can be replaced by $(=CRR')$, where R and R' are hydrocarbon groups and together can form a cyclic structure. For example, a bis(cyclopentyl) complex generates a cyclopentylidene moiety. These compounds are catalysts for the metathesis of ordinary olefins (hydrocarbons), especially functionalized olefins, in the homogeneous phase. this method is more advantageous than prior methods because it requires a limited number of reaction steps, shorter reaction times, and lower cost starting materials. Moreover, this reaction provides for the easy synthesis of metathesis catalysts in the presence of an olefin metathesizable compound.

A principal object of the present invention is to provide olefin metathesis catalyst precursors that require only the input of energy and no chemical activator. Other advantages associated with these catalyst precursors are (i) the catalyst can be generated in situ either in neat monomer or, if desired, in a solvent, (ii) the catalyst can be synthesized very easily using low cost materials in a limited number of steps, (iii) the catalysts provide a simple, inexpensive, convenient preparative route to metathesis catalysts, and (iv) olefin metathesis thermoset polymers containing low levels of halogen can be produced.

DETAILED DESCRIPTION OF THE INVENTION

The olefin metathesis catalyst precursors of this invention have the following structural formula:

$$M(Y)(OR^2)_x(R^3)y(X)_zL_s \qquad (I)$$

wherein M is molybdenum or tungsten; Y is oxygen or $NR^1$; $R^1$, $R^2$ and $R^3$ are the same or different and are selected from alkyl, cycloalkyl, cycloalkenyl, polycycloalkyl, polycycloalkenyl, haloalkyl, haloaralkyl, substituted or unsubstituted aralkyl and aryl groups, and silicon-containing analogs thereof; X is halogen, preferably chlorine or bromine, L is a Lewis base; s=0 or 1; x+y+z=4, and y≧1. In the case where x=2 or more, two $OR^2$ groups can be replaced by a chelating phenolate, catecholate, binaphtholate or chelating alcoholate ligand $(OR^2)_2$, pinacolato, benzopinacolato, and glycolate ligands.

The term "polycycloalkyl" refers to groups containing two or more rings that share two or more carbon atoms, e.g., norbornane and adamantane. The term "cycloalkenyl" refers to cyclic groups containing unsaturation, i.e., cyclopentenyl. The term "polycycloalkenyl" refers to compounds containing two or more rings that share two or more atoms and also contain unsaturation, i.e., dicyclopentenyl. Silicon analogs of the carbon-containing groups listed for $R^1$, $R^2$, and $R^3$ contain silicon atoms in place of one or more carbon atoms. For example, the silicon analog of the neopentyl moiety $(Me_3CCH_2—)$ is the trimethylsilyl group $(Me_3SiCH_2—)$.

The term aryl is employed here to denote a radical derived from a hydrocarbon, having solely aromatic unsaturation in six-membered carbocyclic rings, by removal of a hydrogen atom from a carbon atom of an aromatic ring. Examples of aryl groups are phenyl, naphthyl, 2,6-diisopropylphenyl, and 2,4,6-trimethylphenyl groups. Examples of araalkyl groups are benzyl and triphenylmethyl groups.

The following is a list of substituents that can be attached to the phenyl ring of the substituted aryl or aralkyl groups: Br, Cl, F, I, $CH_3$, $OCH_3$, $SCH_3$, $OC_2H_5$, cyclo-$C_3H_5$, $CF_3$, $OCF_3$, $NMe_2$, $SO_2Me$, $C_6H_5$, $OC_6H_5$, and 1–20 carbon alkyl groups, where Me is a methyl group.

The preferred substituents are selected from methyl, ethyl, propyl, isopropyl, butyl, tert-butyl, sec-butyl, hexyl, cyclohexyl, heptyl, octyl, nonyl, decyl, dodecyl, isopropenyl, phenyl, bromo, chloro, fluoro, ethoxy, methoxy, butoxy, octyloxy, hexadecyloxy, tetradecyloxy, octadecyloxy, pentoxy, phenoxy, cyclopropyl, trifluoromethyl ($CF_3$), trifluoromethyloxy ($OCF_3$), 1,1,2,2-tetrafluoroethoxy ($OCF_2CF_2H$), haloalkyl, dimethylamino ($NMe_2$), methyl sulfonyl ($SO_2Me$), trifluoromethyl sulfonyl ($SO_2CF_3$), aryl sulfonyl ($SO_2Ar$), and benzyl ($CH_2C_6H_5$).

Preferred substituted phenyl groups are 2,6-dimethylphenyl, 2,6-dichlorophenyl, 2,6-diisopropylphenyl, 2,6-dibromophenyl, 2,6-difluorophenyl, 2,6-bis(trifluoromethyl)phenyl, 2,6-bis(trifluoromethoxy)phenyl, 3,5-bis(trifluoromethoxy)phenyl, 2,6-dimethoxyphenyl, 2-tert-butylphenyl, 2,5-di-tert-butylphenyl, 2,3,4,5,6-pentabromophenyl, 2-bromo-4,6-dimethylphenyl, 4-methylphenyl, 4-methoxy-2-methylphenyl, 2-tert-butyl-6-methylphenyl, 2-chloro-6-methylphenyl, and 2-methoxy-5-chlorophenyl.

Referring to (I), $R^1$ is preferably selected from ethyl, tert-butyl, tert-octyl, perfluoro-tert-butyl (($CF_3)_3C$), perfluoro-2-methyl-2-pentyl, phenyl, 4-terto-ctylphenyl, 2,6-dimethylphenyl, 2,4,6-trimethylphenyl, pentafluorophenyl, tri-tert-butylsilyl, triphenylmethyl, triphenylsilyl, 2,6-diisopropylphenyl, 2,6-dichlorophenyl, 2,6-dibromophenyl, 1-adamantyl, and 2-tert-butylphenyl.

$R^2$ is preferably selected from tert-butyl, trifluoro-tert-butyl (($CF_3$) ($CH_3)_2C$), hexafluoro-tert-butyl (($CF_3)_2(CH_3)C$), perfluoro-tert-butyl (($CF_3)_3C$), neopentyl ($CH_2CMe_3$), neophyl ($CH_2CMe_2Ph$), where Ph=phenyl, perfluoro-2-methyl-2-pentyl, 2,6-dimethylphenyl, 2,6-diphenylphenyl, 2,4,6-trimethylphenyl, pentabromophenyl, pentafluorophenyl, trimethylsilyl, tri-tert-butylsilyl, triphenylsilyl, 2,6-diisopropylphenyl, 2,6-dibromophenyl, 2,6-dichlorophenyl, 2,4-dichloro-6-methylphenyl, 2,6-dibromo-4-chlorophenyl, 3,5-bis (trifluoromethyl) phenyl, 2,6-bis(trifluoromethoxy)phenyl, 2,6-bis(trifluoromethyl)phenyl, 2,6-dibromo-4-chlorophenyl, 2,6-dibromo-4-methylphenyl, 2,6-dibromo-4-tert-butylphenyl, 2,6-dibromo-4-tert-octylphenyl, 2,6-dibromophenyl, 2,6-dichloro-4-methylphenyl, 2,6-dichloro-4-methylsulfonylphenyl, 2,6-dichloro-4-tert-butylphenyl, or 2,6-dichloro-4-tert-octylphenyl.

$R^3$ is preferably selected from neopentyl ($CH_2CMe_3$), neophyl ($CH_2CMe_2Ph$), trimethylsilylmethyl ($CH_2SiMe_3$), norbornyl, methyl, benzyl, and dicyclopentenyl. X is preferably chlorine or bromine, and L is preferably diethyl ether; acetonitrile; 4,4,'-dimethyl-2,2'-bipyridine; 2,2'-bipyridine; 1,10-phenanthroline; dimethoxyethane; diethylene glycol dimethyl ether (diglyme); phosphorus compounds having the formula $PR_3$ and $R_2PCH_2CH_2PR_2$, in which R is an alkyl or aryl group; 1,4-diaza-1,3-butadienes having the formula RN=CH—Ch=N—R, where R is an alkyl, substituted or unsubstituted aryl or aralkyl group; tetrahydrofuran; quinuclidine; pyridine; 4-phenylpyridine; tert-butylamine; 1-adamantylamine; aniline; 2,6-diisopropylaniline; 2,6-dimethylaniline, and 2-tert-butylaniline.

A Lewis base is a compound that is capable of donating a pair of electrons. Suitable Lewis bases, include, for example, diethyl ether; acetonitrile; tetrahydrofuran; 2,2'-bipyridine; 4,4'-dimethyl-2,2'-bipyridine; 1,10-phenanthroline; pyridine; dimethoxyethane; diethylene glycol dimethyl ether (diglyme); quinuclidine; 2-tert-butylaniline; 4-phenylpyridine; tert-butylamine; 1-adamantylamine; aniline; 2,6-diisopropylaniline; 2,6-dimethylaniline; phosphorus compounds having the formula $PR_3$ and $R_2PCH_2CH_2PR_2$, in which R is an alkyl or aryl group, and 1,4-diaza-1,3-butadienes having the formula RN=CH—Ch=NR, where R is an alkyl, substituted or unsubstituted aryl or aralkyl group.

Bidentate ligands, i.e., $(OR^2)_2$ in formula (I), include, for example, chelating phenolate, catecholate, binaphtholate, or chelating alcoholate ligands, and are selected from the group consisting of 3,5-di-tert-butylcatechol; catechol; binaphtholate; pinacol ($HOC(CH_3)_2C(CH_3)_2OH$); perfluoropinacol ($HOC(CF_3)_2C(CF_3)_2OH$); benzopinacol ($HOCPh_2CPh_2OH$); 2,2'-methylenebis (4-methyl-6-butylphenol); 2,2'-methylenebis(4-chlorophenol); 2,2'-methylenebis-4-ethyl-6-butylphenol); 4,4'-methylenebis(2,6-di-tert-butylphenol); 2,2'-ethylenebis (4,6-di-tert-butylphenol); methylenebis(4-ethyl-6-(1-methylcyclohexyl) phenol; 4,4'-butylidenebis(6-tert-butyl-3-methylphenol); 4,4'-thiobis(6-tert-butyl-3-methylphenol); 4,4'-methylenebis(2,6-dimethylphenol); 1,1'-thiobis(2-naphthol); 2,2'-thiobis(4-methyl-6-tert-butylphenol); 2,2'-isobutylidenebis(4,6-dimethylphenol), and 2,2'-methylenebis(4-methyl-6-cyclohexyl)phenol).

Preferred metathesis catalyst precursors include $W(NC_6H_5)$ $(CH_2CMe_3)_4$, $W(NC_6H_5)$ $(CH_2SiMe_3)_4$, $W(NC_6H_5)$ $(CH_2SiMe_3)_3Cl$, $WO(CH_2CMe_3)_4$, $WO(OCH_2CMe_3)_2(CH_2CMe_3)_2$, $WO(OCH_3CMe_3)_2(CH_2CMe_2Ph)_2$, $W(NC_6H_3-2,6-i-Pr_2)$ $(OCMe_3)_2(CH_2CMe_2Ph)_2$, $W(NC_6H_3-2,6-i-Pr_2)$ $(OCMe(CF_3)_2)_2(CH_2CMe_2Ph)_2$, $W(NC_6H_3-2,6-i-Pr_2)$ $(OCMe(CF_3)_2)_2(CH_2CMe_3)_2$, $W(NC_6H_3-2,6-i-Pr_2)$ $(OC_6H_3-2,6-i-Pr_2)_3(CH_2CMe_2Ph)_2$, $W(NC_6H_32,6-i-Pr_2)$ $(OC_6H_3-2,6-i-Pr_2)_2(CH_2CMe_2Ph)_2$, $W(NC_6H_3-2,6-i-Pr_2)$ $(OCMe_3)_2(CH_2CMe_3)_2$, $W(NC_6H_5)$ $(OCMe_3)_2(CH_2CMe_3)_2$, $W(NC_6H_3-2,6-i-Pr_2)$ $(OC_5H_3-2,6-i-Pr_2)_2(CH_2CMe_3)_2$, Mo $(NC_6H_3-2,6-i-Pr_2)$ $(OCH(CF_3)_2)_2(CH_2CMe_3)_2$, $Mo(NC_6H_3-2,6-i-Pr_2)$ $(OCH(CF_3)_2)_2(CH_2CMe_3)_2(NH_2CMe_3)$, $Mo(NC_6H_3-2,6-i-Pr_2)$ $(OCH(CF_3)_2)_2(CH_2CMe_2Ph)_2$, $Mo(NC_6H_3-2,6-i-Pr_2)$ $(OC_6F_5)_2(CH_2CMe_2Ph)_2(NH_2CMe_3)$, $Mo(NC_6H_3-2,6-i-Pr_2)$ $(OC_6F_6)_2(CH_2CMe_3)_2(NH_2CMe_3)$, Mo $(NCMe_3)$ $(OC_6F_6)_2(CH_2CMe_3)_2(NH_2CMe_3)$, $W(NC_6H_3-2,6-i-Pr_2)$ $Cl_2$(norbornyl)$_2$, $WO(OC_6H_3-2,6-i-Pr_2)$ $Cl_2$(dicyclopentenyl)$_2$, $WO(OC_6H_3-2,6-Cl_2)$ $C_{12}$(dicyclopentenyl)$_2$ and $WO(OC_6H_3-2,6-i-Pr_2)_3(CH_2)$, where Me is a methyl group, Ph is a phenyl group, and i-Pr is an isopropyl group.

A preferred method for preparing catalyst precursors of the type $M(Y)$ $(OR^2)_2(R^3)_2$ is to react $M(Y)$ $(OR^2)_4$ with two equivalents of an alkylating agent containing $R^3$ groups, preferably in an inert atmosphere. Suitable alkylating agents include alkyl lithiums ($R^3Li$); Grignard reagents ($R^3MgCl$), dialkylmagnesiums (($R^3)_2Mg$), and dialkyl zincs (($R^3)_2Zn$). Most preferred are Grignard reagents, for example, neopentylmagnesium chloride and neophylmagnesium chloride. A Lewis base can optionally be present in the reaction mixture.

AS an example of the synthesis described above, tungsten(VI) oxytetrachloride-based catalyst precursors, e.g., $WO(OCH_2CMe_3)_2(CH_2CMe_2ph)_2$, can be prepared by reacting $WO(OCH_2CMe_3)_4$ (generated from $WOCl_4$ and neopentanol) with neophylmagnesium Grignard. Fewer side reactions occur compared to prior synthesis methods where $WO(OCH_2CMe_3)_2Cl_2$ is reacted with an alkylating agent, e.g., RMgX, and a much higher yield of pure product is therefore achieved. This route can be employed when using chelating ligand groups such as $W(Y)$ (O—O) $(OR)_2$, and when tungsten-imido complexes are desired. For example, $W(NR^1)$ $(OR^2)_2(R_3)_2$ is prepared by reacting $W(NR^1)$ $(OR^2)_4$ with $R^3MgCl$.

In addition, the present invention also encompasses within its scope a novel preparative method for one particular class of catalysts capable of metathesizing an olefin, the catalysts having the formula:

$$M(=CHR^4)(NR^1)(OR^2)_2L_s \qquad (II)$$

wherein M is molybdenum or tungsten; $R^1$ and $R^2$ are the same or different and are selected from alkyl, cycloalkyl, cycloalkenyl, polycycloalkyl, polycycloalkenyl, haloalkyl, haloaralkyl, substituted or unsubstituted aryl and aralkyl groups, or silicon-containing analogs thereof; $R^4$ is an alkyl, aryl, or aralkyl group; L is a Lewis base, and s is 0 or 1.

$R^1$ is preferably selected from ethyl, tert-butyl, perfluoro-2-methyl-2-pentyl, 1-adamantyl, phenyl, 2,6-dimethylphenyl, 2,4,6-trimethylphenyl, pentafluorophenyl, tri-tert-butylsilyl, triphenylmethyl, triphenylsilyl, 2,6-diisopropylphenyl, 2,6-dichlorophenyl, and 2-tert-butyl phenyl groups.

$R^2$ is preferably selected from tert-butyl, trifluoro-tert-butyl (($CF_3$) ($CH_3$)$_2$C), hexafluoro-tert-butyl (($CF_3$)$_2$($CH_3$)C), perfluoro-tert-butyl (($CF_3$)$_3$C), neopentyl ($CH_2CMe_3$), neophyl ($CH_2CMe_2Ph$, where Ph=phenyl), perfluoro-2-methyl-2-pentyl, 2,6-dimethylphenyl, 2,6-diphenylphenyl, 2,4,6-trimethylphenyl, pentafluorophenyl, trimethylsilyl, tri-tert-butylsilyl, triphenylsilyl, 2,6-diisopropylphenyl, and 2,6-dichlorophenyl groups.

$R^4$ is preferably hydrogen or a phenyl ($C_6H_5$), tert-butyl ($CMe_3$), dimethylphenylmethyl ($Me_2PhC$), or trimethylsilyl ($Me_3Si$) group. If the catalyst generation is performed in an olefin metathesizable monomer, $R^4$ can also represent any substituent that results from the initial reaction between the $M=CR_4$ complex and the olefin that is being metathesized. When $R^3$ is a cycloalkyl, polycycloalkyl, cycloalkenyl, or polycycloalkenyl group, then (=$CHR^4$) can be replaced by (=CRR'), where R and R' are hydrocarbon groups and together can form a cyclic structure. For example, a bis(cyclopentyl) complex generates a cyclopentylidene moiety.

The compounds (II) can be prepared by supplying energy to a mixture of (1) the catalyst precursor (I) where z is 0; and (2) a solvent, a metathesizable olefin, or a mixture of the two. An intramolecular reaction occurs in solution to yield $M(=CHR^4)(NR^1)(OR^2)_2L_s$. The most preferred source of energy for activating compound (I) is heat. However, laser, sound or microwave radiation can also be used. The most preferred groups are W and Mo for M; $CH_2CMe_3$, $CH_2CMe_2Ph$, $CMe(CF_3)_2$ and $C(CF_3)_2$ for $R^2$, and neopentyl, neophyl, or trimethylsilylmethyl for $R^3$.

Transformation of the catalyst precursor (I) to an active metathesis catalyst can be performed over a wide range of temperatures. The reaction can be conducted from about −78° C. to about 200° C., preferably from about −40° C. to about 150° C., and most preferably from about 0° C. to about 120° C.

As an example of the synthesis described above, the highly reactive tungsten alkylidene, W(=$CHCMe_2Ph$) ($NC_6H_3$-2,6i-$Pr_2$) ($OCMe_3$)$_2$, can be prepared in a one pot, four step process starting from tungsten oxytetrachloride ($WOCl_4$). The reaction sequence is shown in the following scheme:

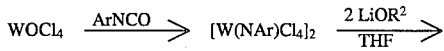

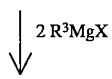

Ar = $C_6H_3$—2,6-i-$Pr_2$
$R^2$ = $CMe_3$
$R^3$ = $CH_2CMe_2Ph$

Tungsten (VI) oxytetrachloride ($WOCl_4$) reacts with 2,6-diisopropylphenyl isocyanate in a solvent (e.g., octane) to give [W($NC_6H_3$-2,6-i-$Pr_2$)$Cl_4$]$_2$. Lithium tert-butoxide (LiOCMe$_3$) reacts with [W($NC_6H_3$-2,6-i-$Pr_2$)$Cl_4$]$_2$ in diethyl ether/tetrahydrofuran to yield W($NC_6H_3$-2,6-i-$Pr_2$)$Cl_2$ ($OCMe_3$)$_2$(THF). Alkylation of W($NC_6H_3$-2,6-i-$Pr_2$)$Cl_2$($OCMe_3$)$_2$(THF) by neophylmagnesium chloride results in the formation of W($NC_6H_3$-2,6-i-$Pr_2$) ($OCMe_3$)$_2$($CH_2CMe_2Ph$)$_2$. These synthesis steps are outlined by R. R. Schrock in *Organometallics*, 1990, vol. 9, pages 2262–2275. Heating a solution of W($NC_6H_3$-2,6-i-$Pr_2$) ($OCMe_3$)$_2$($CH_2CMe_2ph$)$_2$ results in the formation of W($NC_6H_3$-2,6-i-$Pr_2$) ($OCMe_3$)$_2$(=$CHCMe_3ph$). The reaction mixture can be filtered after thermolysis to give a solution of alkylidene. The reaction product can be retained in solution or isolated as a solid by the evaporation of volatiles from the solution using distillation techniques.

The catalyst precursor system of this invention is suitable for the metathesis of an olefin or a mixture of olefins. "Metathesis" includes simple metathesis of olefins, acyclic diene metathesis (ADMET), ring opening metathesis polymerization (ROMP), ring closure, and depolymerization reactions.

In the present invention, olefin metathesis is accomplished by combining the following ingredients and supplying energy to the mixture:

(i) at least one olefin metathesis catalyst precursor having the formula (I), and (ii) at least one olefinic compound that is capable of adding to the alkylidene moiety generated from the olefin metathesis catalyst precursor to generate a new alkylidene substituent capable of sustaining olefin metathesis activity, e.g., norbornene.

The most preferred source of energy is heat. However, laser, sound, or microwave radiation can also be used.

When employing the catalyst precursors in ADMET chemistry, the molar ratio of monomer to metal is preferably about 50:1 to about 10,000:1, most preferably about 100:1 to about 1,000:1. In the olefin metathesis of simple olefins, such as methyl oleate and cis-2-pentene, a monomer to catalyst precursor molar ratio as low as possible is preferred, i.e., 50:1 to 500:1.

Suitable olefin metathesizable substrates include acyclic olefins, cyclic olefins, polycyclic olefins, and α,ω-diolefins. Specific examples include, for example, ethylene, cis-2-pentene, trans-2-pentene, cis-3-hexene, cis-5-decene, methyl oleate (cis-methyl-9-octadecenoate), ethyl oleate, 4-pentenyl acetate, pentadec-1-ene, dec-1-ene, 2-methylbut-2-ene, trimethylvinylsilane, allyltrimethylsilane, and styrene.

Monomers suitable for ADMET chemistry include 1,5-hexadiene, 1,9-decadiene, ethylene diundecenoate, bis(hexenyl)ether, 2,5-dihydrofuran, diallyl ether, diallyldimethylsilane, 4,4,7,7-tetramethyl-4,7-disiladeca-1,9-diene, 1,4-bis(allyldimethylsilyl)benzene, 1,4-benzenedicarboxylic bis(1-hexenyl) ester, 1,4-benzenedicarboxylic bis(1-pentenyl) ester, 1,4-benzenedicarboxylic bis(1-butenyl) ester, and 1-hexenyl-1-pentanoate, trivinylcyclohexane, divinylcyclohexane, and 1,4-divinylbenzene.

The metathesis reaction is preferably carried out in the absence of a solvent. However, a solvent can be present. Suitable solvents include, for example, pentane, hexane, dichloromethane, methylcyclohexane, benzene, chlorobenzene, and toluene. The reaction can be conducted at about 0° C. to about 200° C., preferably about 25° C. to about 150° C., and most preferably about 40° C. to about 120° C.

Cyclic olefins can be metathesis polymerized to a high polymer yield in bulk (neat monomer) or in solution using the catalyst precursor of this invention. The metathesis polymers can be either thermoset or thermoplastic polymers. A thermoplastic polymer is one that can be repeatedly softened by heating and hardened by cooling through a temperature that is characteristic of the polymer and that in the softened state can be shaped by flow into articles by molding or extrusion. Thermoplastic polymeric molecules are linear or branched and as a rule are soluble in specific organic solvents. A thermoset polymer is one that, after having been cured by heat or by other means, is substantially infusible or insoluble. Crosslinked (or cured) polymers can be swelled by organic solvents but cannot be dissolved by them without decomposition.

Preferred cyclic olefin monomers and comonomers are those of the norbornene type that can be represented by the structural formulas

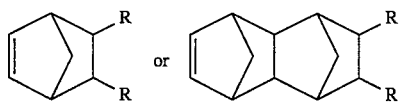

in which each R is selected independently from hydrogen, $C_{1-20}$ alkyl, $C_{1-20}$ alkenyl, and aryl groups, and saturated or unsaturated cyclic hydrocarbon groups in which the R groups are linked together through carbon atoms.

Included in such monomers and comonomers are endo- and exo-dicyclopentadiene (DCPD), symmetrical and unsymmetrical trimers and tetramers of cyclopentadiene, higher order cyclopentadiene oligomers, 2-norbornene, 1-methyl-2-norbornene, 5-methyl-2-norbornene, 5,6-dimethyl-2-norbornene, 5-butyl-2-norbornene, 5-hexylnorbornene, 7-methylnorbornene, vinylnorbornene, ethylidenenorbornene, 5-(2-propenyl)-norbornene, norbornadiene, 5,8-methylene-5a,8a-dihydrofluorene, exo-trans-exo-pentacyclo[8.2.1.1$^{4,7}$.0$^{2,9}$.0$^{3,8}$]tetradeca-5,11-diene, 5,6-acenaphthalenenorbornene, cyclohexenylnorbornene, dimethanohexahydronaphthalene, dimethanooctahydronaphthalene, alkyl substituted derivatives of these cycloolefins and mixtures thereof.

Other suitable polymerizable olefin metathesizable substrates include cyclobutene, cyclobutadiene, cyclopentene, cyclooctene, cycloheptene, cyclododecene, 1,5-cyclooctadiene, cyclododecadiene, and cyclododecatriene.

Additional suitable polymerizable olefin metathesizable substrates include those reported by R. R. Schrock et al. in *Macromolecules*, Vol. 24, 1991, p. 4495–4502; R. R. Schrock in *Accounts of Chemical Research*, Vol. 23, 1990, 158–165, and R. R. Schrock in *The Strem Chemiker*, Vol. XIV (No. 1) Oct. 1992, p. 1–6 (Strem Chemicals, Inc.). Other functionalized monomers include: 2-norbornene-5-carbonitrile, 5-norborn-2-yl acetate, 5-exo-methoxycarbonylnorbornene, endo,endo-5,6-dimethoxynorbornene, 5-endo-methoxycarbonylnorbornene, endo,endo-5,6-dimethoxynorbornene, 5,6-exo-, endo-bis(methoxycarbonyl)norbornene, 5,6-exo-, exo-bis(methoxycarbonyl)norbornene, 5,6-endo-, endo-bis(methoxycarbonyl)norbornene, endo,endo-5,6-dimethoxynorbornene, endo,endo-5,6-dicarbomethoxynorbornene, 2,3-dimethoxynorbornadiene, 5,6-bis(chloromethyl)bicyclo[2.2.1]hepta-2-ene, 2,3-endo-cis-diacetoxy-7-oxanorbornene, 2,3-bistrifluoromethyl-7-oxabicyclo[2.2.1]hepta-2,5-diene, 2,3-dicarbomethoxy-7-oxabicyclo[2.2.1]hepta-2,5-diene, 7-oxabenzonorbornadiene, 2,3-trans-dicyano-7-oxanorborn-5-ene, 5-tris(ethoxy)silylnorbornene, 2-dimethylsilylbicyclo[2.2.1]hepta-2,5-diene, 2,3-bistrifluoromethylbicyclo([2.2.1]hepta-2,5-diene, 5-fluoro-5-pentafluoroethyl-6-,6-bis(trifluoromethyl)bicyclo[2.2.1]hept-2-ene, 5,6-difluoro-5-heptatafluoroisopropyl-6-trifluoromethyl)bicyclo[2.2.1]hept-2-ene, 2,3,3,4,4,5,5,6-octafluorotricyclo[5.2.1.O]dec-8-ene, 2,3 -bis(trifluoromethyl)-7-oxabicyclo[2.2.1]hept-2,5-diene, and 5-trifluoromethylbicyclo[2.2.1]hept-2-ene.

The monomers used should preferably be of the highest purity, containing less than 2% impurities. The endo/exo DCPD used in the following examples was about 98–99% pure monomer. Other monomers or comonomers employed in the practice of this invention should be about this degree of purity. However, the catalysts of this invention can polymerize less pure grades of olefin metathesizable monomers when the appropriate tungsten and molybdenum compounds are employed.

For simple olefin metathesis and polymerization (ADMET and ROMP) reactions performed in solution, the preferred process is to mix the olefin metathesizable species with the olefin metathesis catalyst precursor, or a mixture of catalyst precursors, in a hydrocarbon solvent. When a liquid olefin metathesizable substrate is employed, a reaction solvent may be omitted. Energy is then supplied to the olefin and olefin metathesis catalyst precursor reaction mixture to convert the catalyst precursor to an olefin metathesis catalyst, and to initiate the olefin metathesis reaction. The reaction products can be recovered by removal of the solvent, if necessary, and separation. When a solid olefin metathesizable substrate is employed, the sample can be dissolved or swollen in solvent. For a solid olefin metathesizable substrate, the process of achieving efficient olefin metathesis includes heating a physical mixture of at least one metathesizable olefin and at least one olefin metathesis catalyst precursor to their fusion temperature, or beyond, and inducing dissolution of the ingredients and metathesis of the substrate.

When appropriate olefinic monomers are employed, bulk polymerization of monomers can be carried out in the absence of solvent. By activating a mixture of at least one olefin metathesis catalyst precursor and at least one olefin metathesizable monomer, the polymerization of acyclic and cycloolefins can be achieved. The polymerization of the monomer can yield films, fibers, and molded articles.

The polymerization of the monomer can be performed in a mold to form a solid object. The polymerizable olefin/olefin metathesis catalyst precursor mixture can be introduced into the mold by injection, resin transfer molding, and pouring of liquids, or by addition as a solid. In the case of solid components, production of an olefin metathesis polymer includes supplying energy to a physical mixture of at least one metathesizable olefin and at least one olefin metathesis catalyst precursor to heat the mixture to its fusion temperature, or beyond, and inducing dissolution of the ingredients and metathesis of the reactive olefin. Typically the mold is heated to between 20° and 150° C.

The olefin metathesis catalyst precursor can be placed on a solid support prior to introduction into the mold cavity. Solid supports can include, for example, glass beads, glass fiber, molecular sieves or powder, glass mat, and carbon fiber. The unicomponent olefin metathesis catalyst precursor can be introduced as an encapsulated species, either as an encapsulated liquid or as a solid, provided that the encapsulating material dissolves when in contact with the polymerizable monomer or melts during the input of energy.

A preferred method for molding an object in a single step is injection molding. A reaction injection molding machine is preferably used for convenience. The process for forming a molded object comprising a metathesis polymer includes (1) introducing at least one olefinic metathesis polymerizable monomer and at least one metathesis catalyst precursor into a mold, (2) activating the catalyst precursor in the mold by an energy input to effect catalyst formation and metathesis polymerization to form a solid object, and (3) removing the solid molded article from the mold.

Alternatively, the generation of the olefin metathesis catalyst from the metathesis catalyst precursor can be achieved by supplying energy to a liquid stream (solvent or polymerizable monomer) of the catalyst precursor prior to the stream entering the mold. Supplying additional energy to the reaction mixture in the mold is optional.

In conventional reaction injection molding processes for dicyclopentadiene and other cycloolefins, two reactant streams, one containing an activator and one containing a conventional metathesis catalyst precursor, and at least one stream containing a polymerizable monomer, are mixed together by impingement mixing, or through a mixhead, and the resultant mixture is then introduced into a mold.

Two or more components are typically employed to form alkylidene complexes, e.g., by the reaction of a metal halide and an alkylating agent (see Klosiewicz, U.S. Pat. Nos. 4,400,340 and 4,520,181). The olefin metathesis precursor (I) Of this invention can be used to improve the monomer to polymer conversions of these conventional in situ-generated catalyst systems. The olefin metathesis precursor (I) of this invention can be introduced as an extra stream into a system containing an activator and a conventional catalyst precursor, or it can be combined with either the activator or the conventional catalyst precursor. Separate streams of catalyst ingredients are preferred. For example, a stream of cycloolefin containing diethylaluminum chloride, a stream of cycloolefin containing $W(NC_6H_3\text{-}2,6\text{-i-}Pr_2)$ $(OC_6H_3\text{-}2,6\text{-i-}Pr_2)_2Cl_2$, and a stream of cycloolefin containing $W(NC_6H_3 2,6\text{-i-}Pr_2)$ $(OCMe_3)_2(CH_2CMe_2Ph)_2$ in either cycloolefin or solvent can be admixed at a mixhead and injected into a mold. In the case of dicyclopentadiene and similarly strained olefins, admixture of an activator and conventional catalyst precursor results in a significant exotherm capable of supplying enough energy to convert the olefin metathesis catalyst precursor (I) of this invention to an olefin metathesis catalyst. Mixtures of activators, conventional catalyst precursors, and the energy-activated olefin metathesis catalyst precursors (I) of this invention, and metathesizable monomers in two or more streams are also within the scope of this invention. Suitable activators are organoalkyl aluminums ($R_3Al$), organoalkylaluminum halides ($R^{3-x}AlX_x$), organoalkylaluminum alkoxides ($R^2(RO)Al$), alkylalkoxyaluminum halides ($R(RO)AlX$), trialkyltin hydrides ($R_3SnH$), triaryltin hydrides ($Ar_3SnH$), alkyltins ($R_4Sn$), aryltins ($Ar_4Sn$), diorganozincs ($R^2Zn$), and Grignard reagents ($RMgX$). Suitable conventional catalyst precursors are selected from those derived from tungsten hexachloride ($WCl_6$), tungsten oxytetrachloride ($WOCl_4$); tungsen organoimidotetrachloride ($W(NR)Cl_2$), alkoxide and aryloxide derivatives of tungsten hexachloride ($WCl_{6-x}(OR)_x$), tungsten oxytetrachloride ($WOCl_{4-x}(OR)_x$), tungsten organoimidotetrachloride ($W(NR)Cl_{4-x}(OR)_x$); organoammonium molydates, and organoammonium tungstates.

A preferred embodiment of the RIM process using the catalyst precursors of this invention (I) involves the polymerization of dicyclopentadiene monomer. For example, by injecting a metathesis catalyst precursor (I)/DCPD stream into a heated mold, the formation of a tough, rigid thermoset polyDCPD (crosslinked polymer) is readily achieved. In this way, a spontaneous polymerization occurs and a polymer containing low residual monomer (<1%, preferably <0.5%) can be obtained. This process for preparing polyDCPD can be modified to use more than one stream. Mixtures of catalyst precursors and metathesis polymerizable monomers in one or more streams are also within the scope of this invention.

The molding of olefin metathesis polymerizable monomers can be achieved using a catalyst precursor to monomer molar ratio of about 100:1 to about 200,000:1 on a molar basis, preferably about 200:1 to about 20,000:1, and most preferably about 500:1 to about 5000:1. For a cycloolefin such as dicyclopentadiene, the ratio of catalyst precursor to monomer will preferably be from about 100:1 to about 200,000:1, more preferably 100:1 to 20,000:1, and most preferably about 1500:1 to about 6000:1.

The preparation of molded articles according to the present invention can be carried out in the presence of additives, such as, for example, solvents, blowing agents, fillers, fibers, pigments, antioxidants, flame retardants, light stabilizers, plasticizers, foaming agents, tougheners, reinforcing agents, and polymeric modifiers and viscosifiers. These components are most conveniently added to the reaction as constituents of one or more of the reaction mixture streams, as liquids or as solutions in the monomer.

In some embodiments of this invention, a preformed elastomer that is soluble in the reactant streams is added to the metathesis-catalyst system in order to increase the impact strength of the polymer. The elastomer is dissolved in either or both of the reactant streams in an amount from about 1 to about 15 weight percent, based on the weight of monomer. Suitable elastomers include, for example, natural rubber, butyl rubber, polyisoprene, polybutadiene, polyisobutylene, ethylene-propylene copolymer, styrene-butadiene-styrene triblock rubber, random styrene-butadiene rubber, styrene-isoprene-styrene triblock rubber, ethylene-propylene-diene terpolymers, ethylene-vinyl acetate and nitrile rubbers. Various polar elastomers can also be used. The amount of elastomer used is determined by its molecular weight and is limited by the viscosity of the resultant streams. Preformed elastomers that are essentially insoluble in the reactant streams can also be used.

When using the energy-activated catalyst precursor (I), the rate of catalyst formation depends only on the initiation temperature, therefore gel and cure times can be controlled by adjusting the polymerization temperature. As the temperature at which the reaction is carried out is increased, the gel and cure times will decrease.

The use of Lewis base rate moderators in this system is optional, resulting in further gel and cure time control. Suitable rate moderators include, for example, tetrahydrofuran (THF), 2-methyltetrahydrofuran (2-Me-THF), diethyl ether (($C_2H_5)_2O$), dimethoxyethane ($CH_3OCH_2CH_2OCH_3$), trimethylphosphine ($PMe_3$) triethylphosphine (PEt3), tributylphosphine (PBu3), tricyclohexylphosphine (PCy3), triphenylphosphine ($PPh_3$), methyldiphenylphosphine ($PMePh_2$), dimethylphenylphosphine (PMe$_2$Ph), trimethyl phosphite (P(OMe)$_3$), triethyl phosphite (P(OEt)$_3$), triisopropyl phosphite (P(O-i-Pr)$_3$), ethyl diphenylphosphinite (P(OEt)Ph$_2$), tributyl phosphite (P(OBu)$_3$), triphenyl phosphite (P(OPh)$_3$), triisopropylphosphine (P-i-Pr$_3$), tri-tert-butylphosphine (P-tert-Bu3), diethyl phenylphosphonite (P(OEt)$_2$Ph), tribenzylphosphine (P(CH$_2$Ph)$_3$), tert-butylamine, pyridine, pyrazine, and quinuclidine. Chelating phosphorus ligands, (R)$_2$P(CH$_2$)$_n$P(R)$_2$, where n≧1 and R=aryl or alkyl, can also be employed.

Olefin metathesis thermoset and thermoplastic polymers can be prepared using the activated catalyst precursors of this invention by RIM or other polymerization processes. These polymers contain only trace levels of inorganic halogen or are free of inorganic halogen, e.g., chloride ion. Metathesis polymers of dicyclopentadiene comprised of greater than or equal to 80% metathesis-catalyzed, polymerized units of dicyclopentadiene have only trace levels of inorganic halogen. A trace level of a halogen element is regarded as values of less than 25 ppm.

In the examples in which polymerization studies are set forth, the following general procedures were followed. All operations were carried out under a dry nitrogen or argon atmosphere or in vacuum either in a Vacuum/Atmospheres HE-43 Dri-Lab fitted with a HE-493 Dri-Train or its equivalent (available from Vacuum/Atmospheres Company, Hawthorne, CA, USA) or using Schlenk techniques. Schlenk techniques are described in *The Manipulation of Air-Sensitive Compounds*, 2nd Edition, D. F. Schriver & M. A. Drezdzon, John Wiley and Sons, Inc., New York, 1986. All liquid transfers must be performed by cannula or syringe to maintain an inert atmosphere. Dicyclopentadiene (DCPD) (98–99%) was used in the polymerization experiments.

Polymerizations were conducted in argon- or nitrogen-flushed test tubes, serum vials, glass bottles, reaction vessels or other molds. In general, the polymerizations were accomplished by adding the catalyst precursor, either in solution or in DCPD, to the activator in dicyclopentadiene. Mixing of the ingredients was accomplished with a vortex mixer, magnetic stirrer, or mechanically. The reaction mixtures were maintained at ambient temperature or placed in a constant temperature bath at 80° C. or higher. Gel times (t$_{gel}$) were estimated by observing the initial viscosity change where the mixture changed from a flowable to a nonflowable mass. The time (t$_{100°\ C.}$ or t$_{180°\ C.}$) was recorded when the polymerization raised the exotherm to 100° C. or 180° C. (depending on the initial temperature of the solution), and to the maximum temperature (t$_{Tmax}$) of the polymerization. The maximum temperature (T$_{max}$) of the polymerization was also recorded. The residual DCPD level in polyDCPD samples was obtained by swelling the sample in toluene to extract the DCPD and determining the amount of unreacted DCPD by gas chromatography using an internal standard of dodecane.

In addition to measuring gel and cure times and residual monomer level in the following examples, a measurement of swell value was made. The swell value is an indication of the degree of crosslinking in the polymer, i.e., lower swell values indicate a higher degree of crosslinking. The swell value was determined by removing a sample of polymer from its polymerization vessel and carefully cutting it into smaller pieces. Burrs were removed, and each piece was weighed to the nearest milligram. The samples were then placed in a volume of toluene (50 ml of toluene for each gram of polymer), heated to reflux for 16 hours (overnight) and cooled. After this time, each sample was removed from the flask and placed in a small dish of fresh toluene. The slices were removed, patted dry, and weighed individually. The swell values were calculated using the following formula: swell (%)=(w$_2$−w$_1$)/w$_1$×100%, where w$_1$=the initial weight of the polyDCPD sample and w$_2$=the weight of the solvent-swollen polyDCPD sample. Since the swell value is an indication of the degree of crosslinking in the polymer, low values are preferred.

EXAMPLE 1

This example describes the preparation of W(NC$_6$H$_3$-2,6-i-Pr$_2$) (OCMe$_3$)$_2$(CH$_2$CMe$_2$Ph)$_2$, where i-Pr is an isopropyl group, Me is a methyl group, and Ph is a phenyl group.

A prechilled (−38° to −45° C.) diethyl ether solution of neophylmagnesium chloride (0.077 moles) was added rapidly by drops over a 15 minute period to a chilled solution (−38° to −45° C.) of W(NC$_6$H$_3$-2,6-i-Pr$_2$)(OCMe$_3$)$_2$Cl$_{12.}$THF (50.07 g, 0.154 moles) in 160 ml of diethyl ether, where THF is tetrahydrofuran. The reaction mixture was stirred at room temperature for 24 hours. The salts were removed from the orange solution by centrifuging, then filtering through Manville Celite® filter-aid (available from Fisher Scientific, Fair Lawn, N.J., U.S.A.) and the filter cake was washed thoroughly with diethyl ether (4×50 ml). An orange solid formed upon concentrating the solution in vacuo. The solids were collected and recrystallized from pentane as bright red-orange crystals. A single crystal X-ray determination was performed on the sample and it was found to be pseudo-square pyramidal in geometry with neophyl and tert-butyl groups disposed in a trans geometry.

EXAMPLE 2

This example describes the preparation of W(NC$_6$H$_3$-2,6-i-Pr$_2$) (OCMe$_3$)$_2$(CH$_2$CMe$_3$)$_2$.

A prechilled (−40° C.) diethyl ether solution of neopentylmagnesium chloride (33.7×10$^{-3}$ moles) was added by drops to a chilled solution (−40° C.) of W(NC$_6$H$_3$-2,6-i-Pr$_2$) (OCMe$_3$)$_2$Cl$_2$THF (10.07 g, 15.53×10$^{-3}$ moles) in 100 ml of diethyl ether, where THF is tetrahydrofuran. The reaction mixture was stirred at room temperature for 60 hours. The solution was evaporated to dryness and the product was removed from the salts by washing the solids thoroughly with diethyl ether and pentane. Successive recrystallization from the original pentane/diethyl ether solution yielded 6.16 g of a yellow orange W(NC$_6$H$_3$-2,6-i-Pr$_2$) (OCMe$_3$)$_2$(CH$_2$CMe$_3$)$_2$ product.

EXAMPLE 3

This example describes the preparation of WO(OCH$_2$CMe$_3$)$_2$(CH$_2$CMe$_3$)$_2$.

WO(OCH$_2$CMe$_3$)$_2$Cl$_2$ was reacted with two molar equivalents of neopentylmagnesium chloride (Me$_3$CCH$_2$MgCl) in diethyl ether at −78° C. Pure WO(OCH$_2$CMe$_3$)$_2$(CH$_2$CMe$_3$)$_2$ was isolated by recrystallization from pentane at −78° C.

EXAMPLE 4

This example describes the preparation of WO(OCH$_2$CMe$_3$)$_2$(CH$_2$CMe$_2$Ph )$_2$.

WO(OCH$_2$CMe$_3$)$_4$ was reacted with two molar equivalents of neophylmagnesium chloride (PhMe$_2$CCH$_2$MgCl) in diethyl ether at −78° C. Pure WO(OCH$_2$CMe$_3$)$_2$(CH$_2$CMe$_2$Ph)$_2$ was isolated from the crude reaction product by recrystallization from cold pentane.

EXAMPLE 5

This example describes the polymerization of dicyclopentadiene using W(NC$_6$H$_3$-2,6-i-Pr$_2$)(OCMe$_2$)$_2$(CH$_2$CMe$_3$ph)$_2$ as the catalyst precursor.

W(NC$_6$H$_3$-2,6-i-Pr$_2$) (OCMe$_3$)$_2$(CH$_2$CMe$_2$Ph)$_2$(0.015 g in 0.3 ml of toluene) was mixed with 5 ml of dicyclopentadiene in a glass test tube. The DCPD:W molar ratio was 2000:1. After mixing the reagents briefly at room temperature, the reaction mixture was heated in a 80° C. oil bath. The following reaction parameters describe the polymerization experiment: T$_{gel}$=18 seconds; t$_{100° C.}$=39 seconds; t$_{180° C.}$=42 seconds; t$_{Tmax}$=56 seconds; and T$_{max}$=203° C. Residual DCPD =0.38%.

EXAMPLE 6

This example describes the polymerization of dicyclopentadiene using W(NC$_6$H$_3$-2,6-i-Pr$_2$)(OCMe$_3$)$_2$(CH$_2$CMe$_2$Ph)$_2$ as the catalyst precursor.

W(NC$_6$H$_3$-2,6-i-Pr$_2$) (OCMe$_3$)$_2$(CH$_2$CMe$_2$Ph)$_2$(0.113 g in 0.4 ml of toluene) was mixed with 100 ml of dicyclopentadiene containing 3 wt % ethylidenenorbornene in a glass bottle. The DCPD:W molar ratio was 2000:1. After mixing the reagents at room temperature for five minutes, the bottle and reaction contents were heated to 80° C. At 14 minutes the reaction mixture was a thick gel. At 21 minutes and 30 seconds the dicyclopentadiene solution had polymerized to a solid block, and the internal temperature was 221° C.

EXAMPLE 7

This example describes the polymerization of dicyclopentadiene using W(NC$_6$H$_3$-2,6-i-Pr$_2$)(OCMe$_3$)$_2$(CH$_2$CMe$_2$Ph)$_2$ as the catalyst precursor.

W(NC$_6$H$_3$-2,6-i-Pr$_2$) (OCMe$_3$)$_2$(CH$_2$CMe$_2$Ph)$_2$ (0.113 g in 0.4 ml of toluene) was mixed with 100 ml of dicyclopentadiene containing 3 wt % ethylidenenorbornene in a glass bottle. The DCPD:W molar ratio was 5000:1. After mixing the reagents at room temperature for five minutes, the bottle and reaction contents were heated to 80° C. At 14 minutes the reaction mixture was a thick gel. At 21 minutes and 30 seconds the dicyclopentadiene solution had polymerized to a solid block, and the internal temperature was 221° C.

EXAMPLE 8

This example describes the polymerization of dicyclopentadiene using W(NC$_6$H$_3$-2,6-i-Pr$_2$)(OCMe$_3$)$_2$(CH$_2$CMe$_2$Ph)$_2$ as the catalyst precursor.

W(NC$_6$H$_3$-2,6-i-Pr$_2$) (OCMe$_3$)$_2$(CH$_2$CMe$_2$Ph)$_2$(0.057 g in 0.4 ml of toluene) was mixed with 100 ml of dicyclopentadiene containing 3 wt % ethylidenenorbornene in a glass bottle. The DCPD:W molar ratio was 10,000:1. After mixing the sample, the bottle and reaction contents were heated to 60° C. After 14 minutes the dicyclopentadiene solution had polymerized to a solid block, and the internal temperature was 213° C.

EXAMPLE 9

This example describes the polymerization of dicyclopentadiene using W(NC$_6$H$_3$-2,6-i-Pr$_2$)(OCMe$_3$)$_2$(CH$_2$CMe$_2$Ph)$_2$ as the catalyst precursor.

W(NC$_6$H$_3$-2,6-i-Pr$_2$) (OCMe$_3$)$_2$(CH$_2$CMe$_2$Ph)$_2$ (0.057 g in 0.4 ml of toluene) was mixed with 100 ml of dicyclopentadiene containing 3 wt % ethylidenenorbornene in a glass bottle. The DCPD:W molar ratio was 10,000:1. After mixing the reaction contents, the mixture was kept at room temperature for 4 hours. No polymerization exotherm was observed. The sample was then heated to 80° C. After 17.5 minutes the dicyclopentadiene solution had polymerized to a solid block, and the internal temperature was 193° C.

EXAMPLE 10

This example describes the polymerization of dicyclopentadiene using W(NC$_6$H$_3$-2,6-i-Pr$_2$)(OCMe$_3$)$_2$(CH$_2$CMe$_2$ph)$_2$ as the catalyst precursor.

W(NC$_6$H$_3$-2,6-i-Pr$_2$) (OCMe$_3$)$_2$(CH$_2$CMe$_2$Ph)$_2$ (0,028 g in 0.4 ml of toluene) was mixed with 100 ml of dicyclopentadiene containing 3 wt % ethylidenenorbornene in a glass bottle. The DCPD:W molar ratio was 20,000:1. After mixing the sample for five minutes at room temperature, the bottle and reaction contents were heated to 80° C. At 16.5 minutes the dicyclopentadiene solution had polymerized to a solid block, and the internal temperature 205° C.

EXAMPLE 11

This example describes the preparation of a chlorine-free dicyclopentadiene polymer using W(NC$_6$H$_3$-2,6-i-Pr$_2$)(OCMe$_3$)$_2$(CH$_2$CMe$_2$Ph)$_2$ as the catalyst precursor.

W(NC$_6$H$_3$-2,6-i-Pr$_2$) (OCMe$_3$)$_2$(CH$_2$CMe$_2$Ph)$_2$ (0.028 g in 0.4 ml of toluene) was mixed with 100 ml of dicyclopentadiene containing 3 wt % ethylidenenorbornene in a glass bottle. The DCPD:W molar ratio was 20,000:1. After mixing the sample for five minutes at room temperature, the bottle and reaction contents were heated to 80° C. At 16.5 minutes the dicyclopentadiene solution had polymerized to a solid block, and the internal temperature was 205° C. When analyzed for chlorine content, the polyDCPD was found to contain 22 ppm. This amount of chlorine is regarded as a trace level of the element and, based on the fact that no chlorine was introduced into the ingredients, this level is regarded as contamination through incidental contact.

EXAMPLE 12

This example describes the polymerization of dicyclopentadiene using W(NC$_6$H$_3$-2,6-i-Pr$_2$)(OCMe$_3$)$_2$(CH$_2$CMe$_2$Ph)$_2$ as the catalyst precursor and a Lewis base reaction rate moderator.

W(NC$_6$H$_3$-2,6-i-Pr$_2$) (OCMe$_3$)$_2$(CH$_2$CMe$_2$Ph)$_2$(0.0.10 g in 0.4 ml of toluene) was mixed with ml of dicyclopentadiene in a glass test tube. The DCPD:W molar ratio was 2000:1. To this mixture was added triethylphosphine (Et$_3$P) (2 eq. per W). After mixing the reagents at room temperature, the reaction contents were heated to 80° C. After 7 seconds the reaction mixture gelled. The polymerization mixture reached 100° C. at 3 minutes 55 seconds and 180° C. at 4 minutes 12 seconds. After 4 minutes and 44 seconds the dicyclopentadiene solution had polymerized to a solid block and the maximum internal temperature was 224° C.

EXAMPLE 13

This example describes the preparation of polydicyclopentadiene plaques by reaction injection molding, using W(NC$_6$H$_3$-2,6-i-Pr$_2$) (OCMe$_3$)$_2$(CH$_2$CMe$_2$Ph)$_2$ as the catalyst precursor.

Using a laboratory scale RIM molding machine, polydicyclopentadiene plaques were made by feeding equal volumes of two streams of DCPD monomer (>98% purity containing 3% ethylidenenorbornene (ENB) as a freezing point depressant) to a mixhead and immediately injecting the catalyst mixture into a heated mold. One stream contained only DCPD and the second contained the catalyst precursor $W(NC_6H_3\text{-}2,6\text{-}i\text{-}Pr_2)(OCMe_3)_2(CH_2CMe_2Ph)_2$ (2.52 g) dissolved in DCPD (865 g DCPD, 3 wt % ENB). The DCPD:W molar ratio was 2000:1. The mixing and mold filling were accomplished within two seconds. The rate of polymerization was determined by the mold temperature as shown in Table 1.

TABLE 1

Effect of Temperature on Cure Times ($t_{Tmax}$)

| Molding Temperature (°C.) | Cure Time (seconds) | Residual Monomer (%) |
|---|---|---|
| 90 | 108 | 1.01 |
| 92 | — | 1.35 |
| 107 | 74 | 2.01 |
| 114 | 43 | 1.46 |
| 135 | 38 | 5.54 |

EXAMPLE 14

This example describes the conversion of $W(NC_6H_3\text{-}2,6\text{-}i\text{-}Pr_2)(OCMe_3)_2(CH_2CMe_2Ph)_2$ to $W(NC_6H_3\text{-}2,6\text{-}i\text{-}Pr_2)(OCMe_3)_2(=CHCMe_2Ph)$ at 60° C.

$W(NC_6H_3\text{-}2,6\text{-}i\text{-}Pr_2)(OCMe_3)_2(CH_2CMe_2Ph)_2$ (50 mg) was dissolved in $d_8$-toluene (1 ml). The solution was heated to 60° C. and the reaction was monitored by proton NMR spectroscopy. The sample converted cleanly to $W(NC_6H_3\text{-}2,6\text{-}i\text{-}Pr_2)(OCMe_3)_2(=CHCMe_2Ph)$ and tert-butylbenzene.

EXAMPLE 15

This example describes the conversion of $W(NC_6H_3\text{-}2,6\text{-}i\text{-}PR2)(OCMe_3)_2(CH_2CMe_2Ph)_2$ to $W(NC_6H_3\text{-}2,6\text{-}i\text{-}Pr_2)(OCMe_3)_2(=CHCMe_2Ph)$ at 70° C.

$W(NC_6H_3\text{-}2,6\text{-}i\text{-}Pr_2)(OCMe_3)_2(CH_2CMe_2Ph)_2$ (50 mg) was dissolved in $d_8$-toluene (1 ml). The solution was heated to 70° C. and the reaction was monitored by proton NMR spectroscopy. The sample converted cleanly to $W(NC_6H_3\text{-}2,6\text{-}i\text{-}Pr_2)(OCMe_3)_2(=CHCMe_2Ph)$ and tert-butylbenzene.

EXAMPLE 16

This example describes the conversion of $W(NC_6H_3\text{-}2,6\text{-}i\text{-}Pr_2)(OCMe_3)_2(CH_2CMe_2Ph)_2$ to $W(NC_6H_3\text{-}2,6\text{-}i\text{-}Pr_2)(OCMe_3)_2(=CHCMe_2Ph)$ at 80° C.

$W(NC_6H_3\text{-}2,6\text{-}i\text{-}Pr_2)(OCMe_3)_2(CH_2CMe_2Ph)_2$ (50 mg) was dissolved in $d_8$-toluene (1 ml). The solution was heated to 80° C. and the reaction was monitored by proton NMR spectroscopy. The sample converted cleanly to $W(NC_6H_3\text{-}2,6\text{-}i\text{-}Pr_2)(OCMe_3)_2(=CHCMe_2Ph)$ and tert-butylbenzene.

EXAMPLE 17

This example describes the conversion of $W(NC_6H_3\text{-}2,6\text{-}i\text{-}Pr_2)(OCMe_3)_2(CH_2CMe_2Ph)_2$ to $W(NC_6H_3\text{-}2,6\text{-}i\text{-}Pr_2)(OCMe_3)_2(=CHCMe_2Ph)$ at 90° C.

$W(NC_6H_3\text{-}2,6\text{-}i\text{-}Pr_2)(OCMe_3)_2(CH_2CMe_2Ph)_2$ (50 mg) was dissolved in $d_8$-toluene (1 ml). The solution was heated to 90° C. and the reaction was monitored by proton NMR spectroscopy. The sample converted cleanly to $W(NC_6H_3\text{-}2,6\text{-}i\text{-}Pr_2)(OCMe_3)_2(=CHCMe_2Ph)$ and tert-butylbenzene.

EXAMPLE 18

This example describes the conversion of $W(NC_6H_3\text{-}2,6\text{-}i\text{-}Pr_2)(OCMe_3)_2(CH_2CMe_2Ph)_2$ to $W(NC_6H_3\text{-}2,6\text{-}i\text{-}Pr_2)(OCMe_3)_2(=CHCMe_2Ph)$ at 100° C.

$W(NC_6H_3\text{-}2,6\text{-}i\text{-}Pr_2)(OCMe_3)_2(CH_2CMe_2Ph)_2$ (50 mg) was dissolved in $d_8$-toluene (1 ml). The solution was heated to 100° C. and the reaction was monitored by proton NMR spectroscopy. The sample converted cleanly to $W(NC_6H_3\text{-}2,6\text{-}i\text{-}Pr_2)(OCMe_3)_2(=CHCMe_2Ph)$ and tert-butylbenzene.

EXAMPLE 19

This example describes the conversion of $W(NC_6H_3\text{-}2,6\text{-}i\text{-}Pr_2)(OCMe_3)_2(CH_2CMe_3)_2$ to $W(NC_6H_3\text{-}2,6\text{-}i\text{-}Pr_2)(OCMe_3)_2(=CHCMe_3)$ at 80° C.

$W(NC_6H_3\text{-}2,6\text{-}i\text{-}Pr_2)(OCMe_3)_2(CH_2CMe_3)_2$ (50 mg) was dissolved in $d_8$-toluene (1 ml). The solution was heated to 80° C. and the reaction was monitored by proton NMR spectroscopy. The sample converted cleanly to $W(NC_6H_3\text{-}2,6\text{-}i\text{-}Pr_2)(OCMe_3)_2(=CHCMe_3)$ and neopentane.

EXAMPLE 20

This example describes the conversion of $W(NC_6H_3\text{-}2,6\text{-}i\text{-}Pr_2)(OCMe_3)_2(CH_2CMe_3)_2$ to $W(NC_6H_3\text{-}2,6\text{-}i\text{-}Pr_2)(OCMe_3)_2(=CHCMe_3)$ at 90° C.

$W(NC_6H_3\text{-}2,6\text{-}i\text{-}Pr_2)(OCMe_3)_2(CH_2CMe_3)_2$ (50 mg) was dissolved in $d_8$-toluene (1 ml). The solution was heated to 90° C. and the reaction was monitored by proton NMR spectroscopy. The sample was seen to cleanly convert to $W(NC_6H_3\text{-}2,6\text{-}i\text{-}Pr_2)(OCMe_3)_2(=CHCMe_3)$ and neopentane.

EXAMPLE 21

This example describes the conversion of $W(NC_6H_3\text{-}2,6\text{-}i\text{-}Pr_2)(OC(CF_3)_3)_2(CH_2CMe_2Ph)_2$ to $W(NC_6H_3\text{-}2,6\text{-}i\text{-}Pr_2)(OC(CF_3)_2)_2(=CHCMe_2Ph)$ at 80° C.

$W(NC_6H_3\text{-}2,6\text{-}i\text{-}Pr_2)(OC(CF_3)_2)_2(CH_2CMe_2Ph)_2$ (50 mg) was dissolved in $d_8$-toluene (1 ml) and heated to 80° C. in an oil bath for one hour. The proton NMR spectrum contained tungsten alkylidene resonances attributable to $W(NC_6H_3\text{-}2,6\text{-}i\text{-}Pr_2)(OCMe(CF_3)_2)_2(=CHCMe_2Ph)$.

EXAMPLE 22

This example describes the preparation of $W(NC_6H_3\text{-}2,6\text{-}i\text{-}Pr_2)(OCMe_3)_2(=CHCMe_2Ph)$ from $W(NC_6H_3\text{-}2,6\text{-}i\text{-}Pr_2)(OCMe_3)_2(CH_2CMe_2Ph)_2$ at 70° C.

$W(NC_6H_3\text{-}2,6\text{-}i\text{-}Pr_2)(OCMe_3)_2(CH_2CMe_2Ph)_2$ (2.82 g) was placed a Schlenk tube and dissolved in hexane (75 ml). The reaction mixture was heated to 70° C. for 4 hours, during which time the solution color changed slightly from red-orange to red-brown. The mixture was stripped of hexane and tert-butylbenzene to recover the reaction product. The proton NMR spectrum of this reaction product showed essentially pure $W(NC_6H_3\text{-}2,6\text{-}i\text{-}Pr_2)(OCMe_3)_2(=CHCMe_2Ph)$. This was confirmed by comparing the spectrum to one obtained for a sample of $W(NC_6H_3\text{-}2,6\text{-}i\text{-}Pr_2)(OCMe_3)_2(=CHCMe_2Ph)$ prepared from $W(NC_6H_3\text{-}2,6\text{-}i\text{-}Pr_2)(=CHCMe_2Ph)Cl_2$ (DME) and two equivalents of lithium tert-butoxide following the method described in R. R. Schrock et al., *Organometallics* 1990, Volume 9, pages 2262–2275.

EXAMPLE 23

This example describes the preparation of $W(NC_6H_3\text{-}2,6\text{-}i\text{-}Pr_2)$ $(OCMe_3)_2(\!=\!CHCMe_2Ph)$ from $W(NC_6H_3\text{-}2,6\text{-}i\text{-}Pr_2)$ $(OCMe_3)_2(CH_2CMe_2Ph)_2$ at 80° C.

$W(NC_6H_3\text{-}2,6\text{-}i\text{-}Pr_2)$ $(OCMe_3)_2(CH_2CMe_2Ph)_2$(3.93 g) was placed in a Schlenk tube and dissolved in toluene (50 ml). The reaction mixture was heated to 80° C. for 2 hours, during which time the solution color changed slightly from red-orange to orange-yellow. The mixture was stripped of solvent to recover a crude reaction product (3.27 g; 100% yield). The proton NMR spectrum of this reaction product showed essentially pure $W(NC_6H_3\text{-}2,6\text{-}i\text{-}Pr_2)$ $(OCMe_3)_2$ $(\!=\!CHCMe_2Ph)$. The solids were recrystallized from pentane at −40° to −50° C. to yield $W(NC_6H_3\text{-}2,6\text{-}i\text{-}Pr_2)$ $(OCMe_3)_2(\!=\!CHCMe_2Ph)$ as a yellow powder (1.76 g; 55.7% yield). The identity of this complex was confirmed by comparing the spectrum to one obtained for a sample of $W(NC_6H_3\text{-}2,6\text{-}i\text{-}Pr_2)$ $(OCMe_3)_2(\!=\!CHCMe_2Ph)$ prepared as described in R. R. Schrock et al., *Organometallics* 1990, Volume 9, pages 2262–2275.

EXAMPLE 24

This example describes the polymerization of DCPD using $WO(OCH_2CMe_3)_2(CH_2CMe_3)_2$ as the catalyst precursor.

$WO(OCH_2CMe_3)_2(CH_2CMe_3)_2$(0.016 g) was placed in a polymerization tube. Dicyclopentadiene (5 ml) was added to achieve a DCPD:W molar ratio of 1050:1. The reaction vessel was then heated to 100° C. and the polymerization reaction was monitored. The following parameters describe the reaction: $t_{gel}$=56 seconds; $t_{100° C.}$=75 seconds; $t_{180°}$=160 seconds; $t_{Tmax}$=182 seconds; and $T_{max}$=236° C. Residual DCPD monomer level=1.99%.

EXAMPLE 25

This example describes the polymerization of DCPD using $WO(OCH_2CMe_3)_2(CH_2CMe_2Ph)_2$ as the catalyst precursor.

$WO(OCH_2CMe_3)_2(CH_2CMe_2Ph)_2$(0.023 g) was placed in a polymerization tube. Dicyclopentadiene (5 ml) was added to achieve a DCPD:W molar ratio of 1000:1. The reaction vessel was then heated to 100° C. and the polymerization reaction was monitored. The following parameters describe the reaction: $t_{gel}$=135 seconds; $t_{180° C.}$=343 seconds; $t_{Tmax}$=364 seconds; and $T_{max}$=223° C. The residual DCPD monomer was 0.39%.

EXAMPLE 26

This example describes the preparation of chlorine-free dicyclopentadiene polymer using $WO(OH_2CMe_3)_2(CH_2CMe_2Ph)_2$ as the catalyst precursor.

$WO(OCH_2CMe_3)_2(CH_2CMe_2Ph)_2$ (0.023 g) was placed in a polymerization tube. Dicyclopentadiene (5 ml) was added to achieve a DCPD:W molar ratio of 1000:1. The reaction vessel was then heated to 100° C. to initiate polymerization. When analyzed for chlorine content, the polyDCPD was found to contain 18 ppm. This amount of chlorine is regarded as a trace level of the element. Since no chlorine was introduced into the ingredients, this level is regarded as incidental.

EXAMPLE 27

This example describes the polymerization of dicyclopentadiene using $W(NC_6H_3\text{-}2,6\text{-}i\text{-}PR2)$ $(OCMe_3)_2(CH_2CMe_3ph)_2$ as the catalyst precursor.

$W(NC_6H_3\text{-}2,6\text{-}i\text{-}Pr_2)$ $(OCMe_3)_2(CH_2CMe_2Ph)_2$(50 mg) was heated in $d_8$-toluene (0.75 g) for 2 hours at 70°–72° C. to generate $W(NC_6H_3\text{-}2,6\text{-}i\text{-}Pr_2)$ $(OCMe_3)_2(\!=\!CHCMe_2Ph)$. The composition of this sample was determined by proton NMR spectroscopy to be predominantly $W(NC_6H_3\text{-}2,6\text{-}i\text{-}Pr_2)$ $(OCMe_3)_2(\!=\!CHCMe_2Ph)$ and tert-butylbenzene, with only a trace of $W(NC_6H_3\text{-}2,6\text{-}i\text{-}Pr_2)$ $(OCMe_3)_2(CH_2CMe_2Ph)_2$. This sample was evaporated to dryness, then redissolved in a minimal amount of toluene. The catalyst concentrate was injected into DCPD (17.8 ml) to give a molar ratio of DCPD:W of 2000:1. The following reaction parameters describe the polymerization experiment performed at room temperature (20° C.): $t_{gel}$=7 seconds; $t_{100° C.}$=69 seconds; $t_{180° C.}$71 seconds; $t_{200° C.}$67 seconds; $T_{max}$=220° C.; and $t_{Tmax}$=107 seconds. The residual DCPD level was 0.12%.

EXAMPLE 28

This example describes the preparation of $W(NC_6H_3\text{-}2,6\text{-}i\text{-}Pr_2)$ $(OCMe(CF_3)_2)_2(\!=\!CHCMe_2Ph)$ from $W(NC_6H_3\text{-}2,6\text{-}i\text{-}Pr_2)$ $(OCMe_3)_2(CH_2CMe_2Ph)_2$.

$W(NC_6H_3\text{-}2,6\text{-}i\text{-}Pr_2)$ $(OCMe_3)_2(CH_2CMe_2Ph)_2$(50 mg) was dissolved in d6-benzene (1 ml). The sample was heated to 70° C. for two hours and the reaction was monitored by proton NMR spectroscopy. The sample converted cleanly to $W(NC_6H_3\text{-}2,6\text{-}i\text{-}Pr_2)$ $(OCMe_3)_2(\!=\!CHCMe_2Ph)$ and tert-butylbenzene. The sample was characterized by a resonance at δ=8.11 ppm for the alkylidene proton, $W\text{-}CHCMe_2Ph$. Two equivalents of hexafluoromethylisopropanol were added to this sample. Displacement of the tert-butoxide groups was monitored by the appearance of a new alkylidene signal at δ=8.92 ppm, corresponding to the newly formed $W(NC_6H_3\text{-}2,6\text{-}i\text{-}Pr_2)$ $(OCMe(CF_3)_2)_2(\!=\!CHCMe_2Ph)$. The identity of this complex was confirmed by comparing the spectrum to one obtained for a sample of $W(NC_6H_3\text{-}2,6\text{-}i\text{-}Pr_2)$ $(OCMe(CF_3)_2)_2(\!=\!CHCMe_2Ph)$ prepared as described in R. R. Schrock et al., *Organometallics*, 1990, Volume 9, pages 2262–2275.

EXAMPLE 29

This example describes the polymerization of 5,5,6-trifluoro-6-trifluoromethylnorbornene using in situ generated $W(NC_6H_3\text{-}2,6\text{-}i\text{-}PR2)$ $(OCMe_3)_2(\!=\!CHCMe_2ph)$ as the catalyst.

$W(NC_6H_3\text{-}2,6\text{-}i\text{-}Pr_2)$ $(OCMe_3)_2(\!=\!CHCMe_2Ph)$ was generated by heating 50 mg of $W(NC_6H_3\text{-}2,6\text{-}i\text{-}Pr_2)$ $(OCMe_3)_2(CH_2CMe_2ph)_2$ in toluene. This catalyst was injected into 5,5,6-trifluoro-6-trifluromethylnorbornene (4 ml). The reaction mixture corresponds to a DCPD:W molar ratio of 500:1. The reaction was monitored at room temperature (32° C.). After a few minutes, the pale yellow liquid contained strings of polymer. The reaction was left at room temperature overnight in an inert atmosphere drybox. Addition of methanol to the monomer solution resulted in the deposition of a small quantity of white polymer.

EXAMPLE 30

This example describes the polymerization of 5,5,6-trifluoro-6-trifluoromethylnorbornene using in situ generated W(NC$_6$H$_3$-2,6-i-Pr$_2$) (OCMe$_3$)$_2$ (=CHCMe$_2$Ph) as the catalyst.

W(NC$_6$H$_3$-2,6-i-Pr$_2$) (OCMe$_3$)$_2$(=CHCMe$_2$Ph) was generated by heating 50 mg of W(NC$_6$H$_3$-2,6-i-Pr$_2$) (OCMe$_3$)$_2$(CH$_2$Me$_2$Ph)$_2$ in toluene. This catalyst was injected into 5,5,6-trifluoro-6-trifluromethylnorbornene (4 ml). This reaction mixture corresponds to a DCPD:W molar ratio of 500:1. The reaction mixture was then placed in a constant temperature bath at 80° C. After a few minutes, the pale yellow liquid had become opaque and contained strings of polymer. The reaction was heated at 80° C. for twelve hours, after which time a solid orange plug had formed.

EXAMPLE 31

This example describes the polymerization of tricyclopentadiene using W(O) (OCH$_2$CMe$_3$)$_2$(CH$_2$Me$_2$Ph)$_2$ as the catalyst precursor.

W(O) (OCH$_2$CMe$_3$)$_2$(CH$_2$CMe$_2$Ph)$_2$(16 mg) was dissolved in a sample of tricyclopentadiene (5.00 g) by warming the sample to the melting point of the cycloolefin. The catalyst precursor to tricyclopentadiene molar ratio was 1:1000. The catalyst precursor dissolved in the monomer within one minute. The solution was heated to 100° C. to induce polymerization. The sample gelled at 163 seconds at 100° C., reached an internal temperature of 180° C. at 630 seconds, and reached a maximum temperature of 196° C. Residual tricyclopentadiene was 2.3%, measured by toluene extraction.

EXAMPLE 32

This example describes the storage of a catalyst precursor/tricyclopentadiene mixture and its subsequent polymerization.

W(O) (OCH$_2$CMe$_3$)$_2$(CH$_2$CMe$_2$Ph)$_2$ (16 mg) was dissolved in tricyclopentadiene (5.00 g) by warming to the melting point of the cycloolefin. The catalyst precursor to tricyclopentadiene molar ratio was 1:1000. The catalyst precursor dissolved in the monomer within one minute. The sample was then allowed to solidify at room temperature and was stored for at least sixteen hours under nitrogen. This sample was then heated to 100° C. to melt the fused material and induce polymerization. The sample slowly thawed and reached the gelled state at 352 seconds, an internal temperature of 180° C. at 647 seconds, and a maximum temperature of 214° C. at 663 seconds. Residual tricyclopentadiene was 4.3% measured by toluene extraction.

EXAMPLE 33

This example describes the preparation of WOCl$_2$((OC$_6$H$_2$-4-Me-6-CMe$_3$)$_2$CH$_2$).

One equivalent of 2,2'-methylenebis(4-methyl-6-tert-butylphenol) (4.98 g, 14.63 mmol) was added to a quantity of WOCL$_4$ (5.0 g, 14.63 mmol) slurried in dried toluene (100 ml). The reaction mixture was sparged to remove the liberated HCl gas. Once the reaction had subsided, the reaction mixture was heated at reflux for one hour. The reaction mixture was then cooled to room temperature and filtered to yield a dark green powder of WOCl$_2$((OC$_6$H$_2$-4-Me-6-CMe$_3$)$_2$CH$_2$). The product was characterized by proton and carbon NMR spectroscopies and by cyclic voltammetry.

EXAMPLE 34

This material describes the preparation of WO((OC$_6$H$_2$-4-Me-6-CMe$_3$)$_2$CH$_2$) (CH$_3$)$_2$.

Two equivalents of methylmagnesium chloride (MeMgCl) were added to a sample of WOCl$_4$ dissolved in diethyl ether, and the mixture was cooled to −78° C. The reaction mixture was warmed slowly to room temperature, during which time the mixture turned from green-black to dark red. The reaction product was then evaporated to dryness. The solids were extracted with copious amounts of pentane. The reaction mixture was filtered to give a blood red pentane solution of WO((OC$_6$H$_{2-4}$-Me-6-CMe$_3$)$_2$CH$_2$) (CH$_3$)$_2$ as well as magnesium salts and other insoluble reaction byproducts. The reaction product WO((OC$_6$H$_2$-4-Me-6-CMe$_3$)$_2$CH$_2$) (CH$_3$)$_2$ was obtained by evaporation of the pentane. The red solid was characterized by proton and carbon-13 NMR spectroscopies and cyclic voltammetry.

EXAMPLE 35

This example describes the polymerization of DCPD using WO((OC$_6$H$_2$-4-Me-6-CMe$_3$)$_2$CH$_2$) (CH$_3$)$_2$ as the catalyst precursor.

A quantity of WO((OC$_6$H$_2$-4-Me-6-CMe$_3$)$_2$CH$_2$) (CH$_3$)$_2$ dissolved in a minimum of dried toluene was added to a volume of DCPD (ml). The reactant stoichiometry was DCPD:W=1000:1 on a molar basis. The sample was heated from room temperature to 80° C. The reaction mixture slowly gelled and polymerized, giving a maximum exotherm of 143° C., and a rubbery red colored plug of polyDCPD.

EXAMPLE 36

This example describes the polymerization of dicyclopentadiene using pure W(NC$_6$H$_3$-2,6-i-Pr$_2$) (OCMe$_3$)$_2$(=CHCMe$_2$Ph) as the catalyst.

The catalyst W(NC$_6$H$_3$-2,6-i-Pr$_2$) (OCMe$_3$)$_2$(=CHCMe$_2$Ph) was prepared according to the synthesis given for W(NC$_6$H$_3$-2,6-i-Pr$_2$) (OCMe$_3$)$_2$(=CHCMe$_2$Ph) in R. R. Schrock et al., *Organometallics*, 1990, Vol. 9, p. 2262–2275.

At 30° C., a toluene solution of W(NC$_6$H$_3$-2,6-i-Pr$_2$) (OCMe$_3$)$_2$(=CHCMe$_2$Ph) (0.023 g in a minimum amount of solvent) was added to a volume of dicyclopentadiene (10 ml). The following parameters describe the polymerization reaction: $t_{gel}$=16 seconds, $t_{100° C.}$66 seconds, $t_{180° C.}$76 seconds, $t_{Tmax}$=108 seconds, and $T_{max}$=217° C. Residual DCPD=0.10%.

It is understood that the preceding examples are presented for illustrative purposes only and do not in any sense limit the scope of the invention as defined by the appended claims.

We claim:

1. A method of activating a catalyst precursor having the formula:

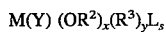

wherein M is molybdenum or tungsten; Y is NR$^1$; R$^1$ and R$^2$ are the same or different and are selected from the group consisting of C$_6$H$_3$-2,6-i-Pr$_2$, CMe$_3$, C(CF$_3$)$_3$, CMe(CF$_3$)$_2$, and CH$_2$CMe$_3$, and R$^3$ is selected from the group consisting of CH$_2$CMe$_2$Ph and CH$_2$CMe$_3$, where Me is a methyl group, Ph is a phenyl group, and i-Pr is an isopropyl group; except when R$^2$ is CMe$_3$, then R$^3$ cannot simultaneously be CH$_2$CMe$_3$, and when R$^3$ is CH$_2$CMe$_3$, then y cannot simultaneously be 4; L is a Lewis base; s is 0 or 1; and x+y=4, which comprises the step of contacting the catalyst precursor with sufficient heat, sound, or electromagnetic radiation to cause the catalyst precursor to convert into a catalyst that is capable of metathesizing an olefin, the catalyst having the formula M(=CHR$^4$) (NR$^1$) (OR$^2$)$_2$L$_s$, wherein R$^4$ is an alkyl, aryl, or aralkyl group, or any substituent that results from an initial reaction between M=CHR$^4$ and the olefin that is being metathesized.

2. A method according to claim 1, wherein the Lewis base is selected from the group consisting of tetrahydrofuran; 2,2'-bipyridine; 4,4'-dimethyl-2,2'-bipyridine; 1,10-phenanthroline, pyridine; dimethoxyethane; diethyl ether; acetonitrile, 4-phenylpyridine; tert-butylamine; 1-adamantylamine; aniline; 2,6-diisopropylaniline; 2,6-dimethylaniline; 2-tert-butylaniline; quinuclidine; phosphorus compounds having the formula PR$_3$ and R$_2$PCH$_2$CH$_2$PR$_2$, in which R is an alkyl or aryl group; diethylene glycol dimethyl ether (diglyme), and 1,4-diaza-1,3-butadienes having the formula RN=CH—CH=NR, where R is an alkyl, substituted or unsubstituted aryl or aralkyl group.

3. A method according to claim 1, wherein the catalyst precursor is selected from the group consisting of W(NC$_6$H$_3$-2,6-i-Pr$_2$) (OCMe$_3$)$_2$(CH$_2$CMe$_2$Ph)$_2$, W(NC$_6$H$_3$-2,6-i-Pr$_2$) (OCH$_2$CMe$_3$)$_2$(CH$_2$CMe$_3$)$_2$, W(NC$_6$H$_3$-2,6-i-Pr$_2$) (OC(CF$_3$)$_3$)$_2$(CH$_2$CMe$_2$Ph)$_2$, W(NC$_6$H$_3$-2,6-i-Pr$_2$) (OCMe(CF$_3$)$_2$)$_2$(CH$_2$CMe$_2$Ph)$_2$, Mo (NC$_6$H$_3$-2,6-i-Pr$_2$) (OCMe$_3$)$_2$(CH$_2$CMe$_2$Ph)$_2$, Mo (NC$_6$H$_3$-2,6-i-Pr$_2$) (OCH$_2$CMe$_3$)$_2$(CH$_2$CMe$_3$)$_2$, Mo (NC$_6$H$_3$-2,6-i-Pr$_2$) (OC(CF$_3$)$_3$)$_2$(CH$_2$CMe$_2$Ph)$_2$, and Mo (NC$_6$H$_3$-2,6-i-Pr$_2$) (OCMe(CF$_3$)$_2$)$_2$(CH$_2$CMe$_2$Ph)$_2$, where Me is a methyl group, Ph is a phenyl group, and i-Pr is an isopropyl group.

4. A method according to claim 1, wherein when x is 2 or more, two OR$^2$ groups can be replaced by a chelating ligand (OR$^2$)$_2$, and wherein the chelating ligands are selected from the group consisting of 3,5-di-tert-butylcatechol; 2,2'-methylenebis(4-chlorophenol); catechol; binaphtholate; pinacol; perfluoropinacol; benzopinacol; 2,2'-methylenebis(4-methyl-6-butylphenol); 2,2'-methylenebis(4-ethyl-6-butylphenol); 4,4'-methylenebis(2,6-tert-butylphenol); 2,2'-ethylenebis (4,6-di-tert-butylphenol); 2,2'-methylenebis(4-ethyl-6-(1-methylcyclohexyl)phenol); 4,4'-butylidenebis(6-tert-butyl-2-methylphenol); 4,4'-thiobis(6-tert-butyl-3-methylphenol; 4,4'-methylenebis(2,6-dimethylphenol); 1,1'-thiobis(2-naphthol); 2,2'-isobutylindenebis(4,6-tert-butylphenol); 2,2'-isobutylindenebis(4,6-dimethylphenol), and 2,2'-methylenebis(4-methyl-6-cyclohexyl)phenol.

5. A method according to claim 1, wherein Y=NC$_6$H$_3$-2,6-i-Pr$_2$, OR$^2$=OCMe$_3$, R$^3$=CH$_2$CMe$_2$Ph, x=2, and y=2, wherein i-Pr is an isopropyl group, Me is a methyl group, and Ph is a phenyl group.

6. A method according to claim 1, wherein Y=NC$_6$H$_3$-2,6-i-Pr$_2$, OR$^2$=OCH$_2$CMe$_3$, R$^3$=CH$_2$CMe$_3$, x=2, and y=2, wherein i-Pr is an isopropyl group, and Me is a methyl group.

7. A method according to claim 1, wherein Y=NC$_6$H$_3$-2,6-i-Pr$_2$, OR$_2$=OCMe(CF$_3$)$_2$, R$^3$=CH$_2$CMe$_2$Ph, x=2, and y=2, wherein Me is a methyl group.

8. The method according to claim 1, wherein R$^4$ is CMe$_3$.

9. The method according to claim 8, wherein R$^2$ is selected from the group consisting of CMe$_3$, C(CF$_3$)$_3$, and CMe(CF$_3$)$_2$.

10. The method according to claim 9, wherein R$^2$ is C$_6$H$_3$-2,6-i-Pr$_2$.

11. The method according to claim 1, wherein R$^4$ is CMe$_2$Ph.

12. The method according to claim 11, wherein is selected from the group consisting of CMe$_3$, C(CF$_3$)$_3$, and CMe(CF$_3$)$_2$.

13. The method according to claim 12, wherein R$^1$ is C$_6$H$_3$-2,6-i-Pr$_2$.

14. The method according to claim 1, wherein the catalyst precursor is W(NC$_6$H$_3$-2,6-i-Pr$_2$) (OCMe$_3$)$_2$(CH$_2$CMe$_2$Ph)$_2$.

15. The method according to claim 1, wherein the catalyst precursor is W(NC$_6$H$_3$-2,6-i-Pr$_2$) (OCH$_2$CMe$_3$)$_2$(CH$_2$CMe$_3$)$_2$.

16. The method according to claim 1, wherein the catalyst precursor is W(NC$_6$H$_3$-2,6-i-Pr$_2$) (OC(CF$_3$)$_3$)$_2$(CH$_2$CMe$_2$Ph)$_2$.

17. The method according to claim 1, wherein the catalyst precursor is W(NC$_6$H$_3$-2,6-i-Pr$_2$) (OCMe(CF$_3$)$_2$)$_2$(CH$_2$CMe$_2$Ph)$_2$.

18. The method according to claim 1, wherein the catalyst precursor is Mo(NC$_6$H$_3$-2,6-i-Pr$_2$) (OCMe$_3$)$_2$(CH$_2$CMe$_2$Ph)$_2$.

19. The method according to claim 1, wherein the catalyst precursor is Mo(NC$_6$H$_3$-2,6-i-Pr$_2$) (OCH$_2$CMe$_3$)$_2$(CH$_2$CMe$_3$)$_2$.

20. The method according to claim 1, wherein the catalyst precursor is Mo(NC$_6$H$_3$-2,6-i-Pr$_2$) (OC(CF$_3$)$_3$)$_2$(CH$_2$CMe$_2$Ph)$_2$.

21. The method according to claim 1, wherein the catalyst precursor is Mo(NC$_6$H$_3$-2,6-i-Pr$_2$) (OCMe(CF$_3$)$_2$)$_2$(CH$_2$CMe$_2$Ph)$_2$.

22. The method according to claim 1, wherein said contacting step is the step of applying heat to the catalyst precursor.

23. The method according to claim 1, wherein said contacting step is the step of applying sound to the catalyst precursor.

24. The method according to claim 1, wherein said contacting step is the step of applying electromagnetic radiation to the catalyst precursor.

25. The method according to claim 1, wherein said contacting step is the step of applying light to the catalyst precursor.

26. The method according to claim 1, wherein said contacting step is the step of applying microwave radiation to the catalyst precursor.

27. A method of activating a catalyst precursor having the formula:

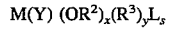

M(Y) (OR$^2$)$_x$(R$^3$)$_y$L$_s$ wherein M is molybdenum or tungsten; Y is oxygen; R$^1$ and R$^2$ are the same or different and are selected from the group consisting of C$_6$H$_3$-2,6-i-Pr$_2$, CMe$_3$, C(CF$_3$)$_3$, CMe(CF$_3$)$_2$, and CH$_2$CMe$_3$; and R$^3$ is selected from the group consisting of CH$_2$CMe$_2$Ph and CH$_2$CMe$_3$, where Me is a methyl group, Ph is a phenyl group, and i-Pr is an isopropyl group; except when R$^2$ is CMe$_3$, then R$^3$ cannot simultaneously be CH$_2$CMe$_3$, and when R$^3$ is CH$_2$CMe$_3$, then y cannot simultaneously be 4; L is a Lewis base; s is 0 or 1; and x+y=4, which comprises the step of contacting the catalyst precursor with sufficient heat, sound, or electromagnetic radiation to activate the catalyst precursor.

28. A method according to claim 27, wherein Y is O, OR$^2$=OCH$_2$CMe$_3$, R$^3$=CH$_2$CMe$_2$Ph, x=2, and y=2.

29. The method according to claim 27, wherein the catalyst precursor is WO(OCH$_2$CMe$_3$)$_2$(CH$_2$CMe$_2$Ph)$_2$.

30. The method according to claim 27, wherein the catalyst precursor is MoO(OCH$_2$CMe$_3$)$_2$(CH$_2$CMe$_2$Ph)$_2$.

31. A method of activating a catalyst precursor having the formula:

$M(Y)(OR^2)_2(R^3)_2L_s$ wherein M is molybdenum or tungsten; Y is $NR^1$; $R^1$, $R^2$, and $R^3$ are the same or different and are selected from the group consisting of alkyl, cycloalkyl, cycloalkenyl, polycycloalkyl, polycycloalkenyl, haloalkyl, haloaralkyl, substituted or unsubstituted aralkyl and aryl groups, and silicon-containing analogs thereof; L is a Lewis base; s is 0 or 1; wherein the two $OR^2$ groups can be replaced by a chelating ligand $(OR^2)_2$, said method comprising the step of contacting the catalyst precursor, in the absence of a chemical activator for the catalyst precursor, with sufficient heat, sound, or electromagnetic radiation to cause the catalyst precursor to convert into a catalyst that is capable of metathesizing an olefin, the catalyst having the formula $M(=CHR^4)(NR^1)(OR^2)_2L_s$, wherein $R^4$ is an alkyl, aryl, or aralkyl group, or any substituent that results from an initial reaction between $M=CHR^4$ and the olefin that is being metathesized.

32. A method of activating a catalyst precursor having the formula:

$M(Y)(OR^2)_2(R^3)_2L_s$ wherein M is molybdenum or tungsten; Y is oxygen; $R^1$, $R^2$, and $R^3$ are the same or different and are selected from the group consisting of alkyl, cycloalkyl, cycloalkenyl, polycycloalkyl, polycycloalkenyl, haloalkyl, haloaralkyl, substituted or unsubstituted aralkyl and aryl groups, and silicon-containing analogs thereof; L is a Lewis base; s is 0 or 1; wherein the two $OR^2$ groups can be replaced by a chelating ligand $(OR^2)_2$, said method comprising the step of contacting the catalyst precursor, in the absence of a chemical activator for the catalyst precursor, with sufficient heat, sound, or electromagnetic radiation to activate the catalyst precursor.

33. A method of activating a catalyst precursor having the formula:

$M(Y)(OR^2)_4(R^3)_yL_s$ wherein M is molybdenum or tungsten; Y is $NR^1$; $R^1$ and $R^2$ are the same or different and are selected from the group consisting of $C_6H_3$-2,6-i-$Pr_2$, $CMe_3$, $C(CF_3)_3$, $CMe(CF_3)_2$, and $CH_2CMe_3$; and $R^3$ is selected from the group consisting of $CH_2CMe_2Ph$ and $CH_2CMe_3$, where Me is a methyl group, Ph is a phenyl group, and i-Pr is an isopropyl group; except when $R^2$ is $CME_3$, then $R^3$ cannot simultaneously be $CH_2CMe_3$, and when $R^3$ is $CH_2CMe_3$, then y cannot simultaneously be 4; L is a Lewis base; s is 0 or 1; and x+y=4, which comprises the step of contacting the catalyst precursor, in the absence of a chemical activator for the catalyst precursor, with sufficient heat, sound, or electromagnetic radiation to cause the catalyst precursor to convert into a catalyst that is capable of metathesizing an olefin, the catalyst having the formula $M(=CHR^4)(NR^1)(OR^2)_2L_s$, wherein $R^4$ is an alkyl, aryl, or aralkyl group, or any substituent that results from an initial reaction between $M=CHR^4$ and the olefin that is being metathesized.

34. A method of activating a catalyst precursor having the formula:

$M(Y)(OR^2)_x(R^3)_yL_s$ wherein M is molybdenum or tungsten; Y is oxygen; $R^1$ and $R^2$ are the same or different and are selected from the group consisting of $C_6H_3$-2,6-i-$Pr_2$, $CMe_3$, $C(CF_3)_3$, $CMe(CF_3)_2$, and $CH_2CMe_3$; and $R^3$ is selected from the group consisting of $CH_2CMe_2Ph$ and $CH_2CMe_3$, where Me is a methyl group, Ph is a phenyl group, and i-Pr is an isopropyl group; except when $R^2$ is $CMe_3$, then $R^3$ cannot simultaneously be $CH_2CMe_3$, and when $R^3$ is $CH_2CMe_3$, then y cannot simultaneously be 4; L is a Lewis base; s is 0 or 1; and x+y=4, which comprises the step of contacting the catalyst precursor, in the absence of a chemical activator for the catalyst precursor, with sufficient heat, sound, or electromagnetic radiation to activate the catalyst precursor.

* * * * *

UNITED STATES PATENT AND TRADEMARK OFFICE
CERTIFICATE OF CORRECTION

PATENT NO. : 5,606,085
DATED : February 25, 1997
INVENTOR(S) : ANDREW BELL, ET AL.

It is certified that error appears in the above-identified patent and that said Letters Patent is hereby corrected as shown below:

On title page,

At [62] (Related U.S. Application Data)

"5,502,228" should read --5,639,900--.

COLUMN 2

Line 31, "(NR$^1$)" should read --(NR$^1$)--;
Line 39, "(NC$_6$H$_3$2,6-i-Pr$_2$)" should read --(NC$_6$H$_3$-2,6-i-Pr$_2$)--; and
Line 43, "(OCMe(CF$_3$)$_2$)$_2$W(NC$_6$H$_3$-2,6-i-Pr$_2$)" should read --(OCMe(CF$_3$)$_2$)$_2$, W(NC$_6$H$_3$-2,6-i-Pr$_2$)--.

COLUMN 3

Line 38, "+y+z=4," should read --x+y+z=4,--.

COLUMN 4

Line 7, "this" should read --This--; and
Line 66, "C$_6$H$_5$," should read --C$_6$H$_5$, CH$_2$C$_6$H$_5$,--.

COLUMN 5

Line 23, "4-terto-ctylphenyl," should read --4-tert-octylphenyl,--.

UNITED STATES PATENT AND TRADEMARK OFFICE
CERTIFICATE OF CORRECTION

PATENT NO. : 5,606,085
DATED : February 25, 1997
INVENTOR(S) : ANDREW BELL, ET AL.

It is certified that error appears in the above-identified patent and that said Letters Patent is hereby corrected as shown below:

COLUMN 6

Line 31, "$(OC_6H_3-2,6-i-Pr_2)_2(CH_2CMe_2Ph)_2,$" should read --$(OC_6H_3-2,6-i-Pr_2)_2(CH_2CMe_2Ph)_2$--;
Line 33, "$(OC_5H_3-2,6-$" should read --$(OC_6H_3-2,6-$--;
Line 40, "$(OC_6F_6)_2$" should read --$(OC_6F_5)_2$--;
Line 43, "$C_{12}(dicyclopentenyl)_2$" should read --$Cl_2(dicyclopentenyl)_2$--, and "$WO(OC_6H_3-2,6-i-Pr_2)_3(CH_2),$" should read --$WO(OC_6H_3-2,6-i-Pr_2)_3(CH_3),$--;
Line 55, "AS" should read --As--; and
Line 57, "$WO(OCH_2CMe_3)_2(CH_2CMe_2ph)_2,$" should read --$WO(OCH_2CMe_3)_2(CH_2CMe_2Ph)_2,$--.

COLUMN 7

Line 34, "$M=CR_4 complex$" should read --$M=CHR^4$ complex--.

COLUMN 8

Line 25, "$(OCMe_3)_2(CH_2CMe_2ph)_2$" should read --$(OCMe_3)_2(CH_2CMe_2Ph)_2$--; and
Line 26, "$(OCMe_3)_2(=CHCMe_3ph).$" should read --$(OCMe_3)_2(=CHCMe_2Ph).$--

COLUMN 10

Line 17, "[5.2.1.0]dec-" should read --[5.2.1.0]dec---.

UNITED STATES PATENT AND TRADEMARK OFFICE
CERTIFICATE OF CORRECTION

PATENT NO. : 5,606,085
DATED : February 25, 1997
INVENTOR(S) : ANDREW BELL, ET AL.

It is certified that error appears in the above-identified patent and that said Letters Patent is hereby corrected as shown below:

COLUMN 11

Line 37, "Of" should read --of--;
       Line 60, "$(R^{3-x}AlX_x)$," should read --$(R_{3-x}AlX_x)$; and
       Line 61, "$(R^2(RO)Al)$," should read --$(R_2(RO)Al)$,--;
       Line 64, "$(R^2Zn)$," should read --$(R_2Zn)$,--.

COLUMN 12

Line 1, "$(W(NR)Cl_2)$," should read --$(W(NR)Cl_4)$,--;
       Line 65, "(PEt3)," should read --$PEt_3$,--; and
       Line 66, "(PBu3)," should read --$(PBu_3)$,--, and "(PCy3)," should read --$(PCy_3)$,--.

COLUMN 13

Line 6, "(P-tert-Bu3)," should read --$(P\text{-}tert\text{-}Bu_3)$,--; and
       Line 15, "choride" should read --chloride--.

COLUMN 14

Line 3, "$(\%)= (w_2-W_1)/W_1 \times 100\%$," should read --$\% = (w_2-w_1)/w_1 \times 100\%$,--; and
       Line 18, "$(OCMe_3)_2Cl_{12} \cdot THF$" should read --$(OCMe_3)_2Cl_2 \cdot THF$--.

UNITED STATES PATENT AND TRADEMARK OFFICE
CERTIFICATE OF CORRECTION

PATENT NO. : 5,606,085
DATED : February 25, 1997
INVENTOR(S) : ANDREW BELL, ET AL.

It is certified that error appears in the above-identified patent and that said Letters Patent is hereby corrected as shown below:

COLUMN 15

Line 4, "$(OCMe_2)_2(CH_2CMe_3ph)_2$" should read --$(OCMe_3)_2(CH_2CMe_2Ph)_2$--; and
Line 11, "$T_{gel} = 18$" should read --$t_{gel} = 18$--.

COLUMN 16

Line 14, "$(OCMe_3)_2(CH_2CMe_2ph)_2$" should read --$(OCMe_3)_2(CH_2CMe_2Ph)_2$--;
Line 15, "0,028" should read --0.028--; and
Line 22, "temperature" should read --temperature was--.

COLUMN 17

Line 41, "i-PR2)" should read --i-$Pr_2$)--.

COLUMN 18

Line 40, "$(OC(CF_3)_3)_2(CH_2CMe_2Ph)_2$to" should read --$(OC(CF_3)_3)_2(CH_2CMe_2Ph)_2$ to--; and
Line 41, "$(OC(CF_3)_2)_2(=CHCMe_2Ph)$" should read --$(OC(CF_3)_3)_2(=CHCMe_2Ph)$--.

UNITED STATES PATENT AND TRADEMARK OFFICE
CERTIFICATE OF CORRECTION

PATENT NO. : 5,606,085
DATED : February 25, 1997
INVENTOR(S) : ANDREW BELL, ET AL.

It is certified that error appears in the above-identified patent and that said Letters Patent is hereby corrected as shown below:

COLUMN 20

Line 4, "W(NC$_6$H$_3$-2,6-i-PR2) (OCMe$_3$)$_2$(CH$_2$CMe$_3$" should read --W(NC$_6$H$_3$-2,6-i-Pr$_2$) (OCMe$_3$)$_2$(CH$_2$CMe$_2$--;
Line 4, "ph)$_2$" should read --Ph)$_2$--;
Line 19, "t$_{180° C.}$71 seconds; t$_{200° C.}$67 seconds;" should read --t$_{180° C.}$=71 seconds; t$_{200° C.}$=67 seconds;--;
Line 31, "d6-benzene" should read --d$_6$-benzene--;
Line 54, "W(NC$_6$H$_3$-2,6-i-PR2)" should read --W(NC$_6$H$_3$-2,6-i-Pr$_2$)--; and
Line 59, "(OCMe$_3$)$_2$(CH$_2$CMe$_2$ph)$_2$" should read --(OCMe$_3$)$_2$(CH$_2$CMe$_2$Ph)$_2$--.

COLUMN 22

Line 12, "WO((OC$_6$H$_{2-4}$-Me-6-CMe$_3$)$_2$CH$_2$)" should read --WO((OC$_6$H$_2$-4-Me-6-CMe$_3$)$_2$CH$_2$)--;
Line 27, "(ml)." should read --(10 ml).--; and
Line 48, "t$_{100° C.}$66 seconds, t$_{180° C.}$76 sec-" should read --t$_{100° C.}$=66 seconds, t$_{180° C.}$=76 sec---.

COLUMN 23

Line 64, "R$^2$" should read --R$^1$--.

COLUMN 24

Line 1, "wherein" should read --wherein R$^2$--; and
Line 24, "(OC(CF$_3$)$_2$)$_2$(CH$_2$CMe$_2$Ph)$_2$·" should read --(OC(CF$_3$)$_3$)$_2$(CH$_2$CMe$_2$Ph)$_2$·--.

UNITED STATES PATENT AND TRADEMARK OFFICE
CERTIFICATE OF CORRECTION

PATENT NO. : 5,606,085

DATED : February 25, 1997

INVENTOR(S) : ANDREW BELL, ET AL.

It is certified that error appears in the above-identified patent and that said Letters Patent is hereby corrected as shown below:

COLUMN 26

Line 1, "$NR^{1;}$" should read --$NR^1$;--; and
    Line 7, "$CME_3$," should read --$CMe_3$,--.

Signed and Sealed this

Fourteenth Day of July, 1998

*Attest:*

*Attesting Officer*

BRUCE LEHMAN

*Commissioner of Patents and Trademarks*